United States Patent
Tompkins et al.

(10) Patent No.: US 11,076,792 B2
(45) Date of Patent: Aug. 3, 2021

(54) ECG PATCH AND METHODS OF USE

(71) Applicant: HMicro, Inc., Fremont, CA (US)

(72) Inventors: Kim Tompkins, San Jose, CA (US);
Thomas Varghese, Bangalore (IN)

(73) Assignee: LIFESIGNALS, INC., Fremont, CA (US)

( * ) Notice: Subject to any disclaimer, the term of this patent is extended or adjusted under 35 U.S.C. 154(b) by 896 days.

(21) Appl. No.: 14/814,436

(22) Filed: Jul. 30, 2015

(65) Prior Publication Data

US 2016/0029906 A1 Feb. 4, 2016

Related U.S. Application Data

(60) Provisional application No. 62/031,079, filed on Jul. 30, 2014, provisional application No. 62/186,277, filed on Jun. 29, 2015.

(51) Int. Cl.
| | |
|---|---|
| *A61B 5/282* | (2021.01) |
| *A61B 5/00* | (2006.01) |
| *A61B 5/0205* | (2006.01) |
| *A61B 5/024* | (2006.01) |
| *A61B 5/08* | (2006.01) |

(52) U.S. Cl.
CPC ............ *A61B 5/282* (2021.01); *A61B 5/0205* (2013.01); *A61B 5/6823* (2013.01); *A61B 5/0002* (2013.01); *A61B 5/0006* (2013.01); *A61B 5/02438* (2013.01); *A61B 5/0816* (2013.01); *A61B 5/684* (2013.01); *A61B 2560/0412* (2013.01); *A61B 2560/0462* (2013.01); *A61B 2560/0468* (2013.01)

(58) Field of Classification Search
CPC .. A61B 5/0205; A61B 5/04085; A61B 5/6823
USPC .......................... 600/301, 393, 483, 508, 509
See application file for complete search history.

(56) References Cited

U.S. PATENT DOCUMENTS

| | | | |
|---|---|---|---|
| 3,786,391 A | | 1/1974 | Mathauser |
| 3,808,577 A | | 4/1974 | Mathauser |
| 3,868,948 A | * | 3/1975 | Graetz ............... A61B 5/04004 600/522 |
| 4,067,342 A | | 1/1978 | Burton |

(Continued)

FOREIGN PATENT DOCUMENTS

| | | |
|---|---|---|
| CN | 101534706 A | 9/2009 |
| CN | 102599901 A | 7/2012 |

(Continued)

OTHER PUBLICATIONS

Office action dated Feb. 8, 2016 for U.S. Appl. No. 14/805,389.

(Continued)

*Primary Examiner* — John R Downey
(74) *Attorney, Agent, or Firm* — Wilson Sonsini Goodrich & Rosati

(57) ABSTRACT

A compact integrated patch may be used to collect physiological data. The patch may be wireless. The patch may be utilized in everyday life as well as in clinical environments. Data acquired by the patch and/or external devices may be interpreted and/or be utilized by healthcare professionals and/or computer algorithms (e.g., third party applications). Data acquired by the patch may be interpreted and be presented for viewing to healthcare professionals and/or ordinary users.

20 Claims, 27 Drawing Sheets

(56) References Cited

U.S. PATENT DOCUMENTS

| | | | |
|---|---|---|---|
| 4,082,086 A | 4/1978 | Page et al. | |
| 4,084,583 A | 4/1978 | Hjort | |
| 4,121,573 A | 10/1978 | Crovella et al. | |
| 4,365,634 A | 12/1982 | Bare et al. | |
| 4,398,545 A | 8/1983 | Wilson | |
| 4,624,263 A * | 11/1986 | Slavin | A61B 5/0436 |
| | | | 600/523 |
| 4,653,503 A | 3/1987 | Heath | |
| 4,705,049 A * | 11/1987 | John | A61B 5/0484 |
| | | | 600/544 |
| 5,168,874 A | 12/1992 | Segalowitz | |
| 5,372,125 A | 12/1994 | Lyons | |
| 5,483,967 A | 1/1996 | Ohtake | |
| 5,578,065 A | 11/1996 | Hattori et al. | |
| 5,634,468 A | 6/1997 | Platt et al. | |
| 5,704,351 A * | 1/1998 | Mortara | A61N 1/3727 |
| | | | 600/382 |
| 5,895,369 A | 4/1999 | Flower | |
| 5,948,006 A | 9/1999 | Mann | |
| 6,104,306 A | 8/2000 | Hogue et al. | |
| 6,117,077 A * | 9/2000 | Del Mar | A61B 5/04085 |
| | | | 600/300 |
| 6,168,568 B1 | 1/2001 | Gavriely | |
| 6,441,747 B1 | 8/2002 | Khair et al. | |
| 6,453,186 B1 | 9/2002 | Lovejoy et al. | |
| 6,456,720 B1 | 9/2002 | Brimhall et al. | |
| 6,814,706 B2 | 11/2004 | Barton et al. | |
| 6,897,788 B2 | 5/2005 | Khair et al. | |
| 6,965,794 B2 | 11/2005 | Brody | |
| 7,156,301 B1 | 1/2007 | Bonalle et al. | |
| 7,206,630 B1 | 4/2007 | Tarler et al. | |
| 7,257,438 B2 | 8/2007 | Kinast | |
| 7,400,298 B2 | 7/2008 | Fogg et al. | |
| 7,486,977 B2 | 2/2009 | Sweitzer et al. | |
| 7,499,739 B2 * | 3/2009 | Sweitzer | A61B 5/0002 |
| | | | 600/323 |
| 7,668,580 B2 | 2/2010 | Shin et al. | |
| 7,796,042 B2 | 9/2010 | Walther et al. | |
| 7,920,096 B2 | 4/2011 | Fogg et al. | |
| 7,969,307 B2 | 6/2011 | Peeters | |
| 7,970,450 B2 | 6/2011 | Kroecker et al. | |
| 8,150,502 B2 | 4/2012 | Kumar et al. | |
| 8,287,386 B2 | 10/2012 | Miller et al. | |
| 8,315,687 B2 | 11/2012 | Cross et al. | |
| 8,611,980 B2 | 12/2013 | Choe et al. | |
| 8,628,020 B2 | 1/2014 | Beck | |
| 8,688,189 B2 | 4/2014 | Shennib | |
| 8,718,742 B2 | 5/2014 | Beck et al. | |
| 8,926,509 B2 | 1/2015 | Magar et al. | |
| 9,019,934 B2 | 4/2015 | Yun et al. | |
| 9,265,435 B2 | 2/2016 | Beck | |
| 2002/0037756 A1 | 3/2002 | Jacobs et al. | |
| 2002/0045836 A1 | 4/2002 | Alkawwas | |
| 2003/0040305 A1 | 2/2003 | Ng et al. | |
| 2003/0069510 A1 | 4/2003 | Semler | |
| 2003/0083584 A1 * | 5/2003 | Yonce | A61B 5/6843 |
| | | | 600/509 |
| 2004/0019288 A1 * | 1/2004 | Kinast | A61B 5/0402 |
| | | | 600/509 |
| 2004/0131897 A1 | 7/2004 | Jenson et al. | |
| 2006/0009691 A1 * | 1/2006 | Yeo | A61B 5/0245 |
| | | | 600/386 |
| 2006/0030782 A1 | 2/2006 | Shennib et al. | |
| 2006/0155183 A1 | 7/2006 | Kroecker et al. | |
| 2006/0264767 A1 * | 11/2006 | Shennib | A61B 5/0006 |
| | | | 600/509 |
| 2007/0060832 A1 | 3/2007 | Levin | |
| 2007/0072443 A1 | 3/2007 | Rohrbach et al. | |
| 2007/0093705 A1 | 4/2007 | Shin et al. | |
| 2007/0179376 A1 | 8/2007 | Gerder | |
| 2007/0293781 A1 | 12/2007 | Sims et al. | |
| 2008/0055045 A1 | 3/2008 | Swan et al. | |
| 2008/0081960 A1 * | 4/2008 | Rantala | A61B 5/04004 |
| | | | 600/301 |
| 2008/0139953 A1 | 6/2008 | Baker et al. | |
| 2008/0186241 A1 | 8/2008 | Christensen | |
| 2008/0221398 A1 * | 9/2008 | Ronchi | A61B 5/1126 |
| | | | 600/301 |
| 2008/0309287 A1 | 12/2008 | Reed | |
| 2009/0036792 A1 | 2/2009 | Deluca et al. | |
| 2009/0073991 A1 | 3/2009 | Landrum et al. | |
| 2009/0221897 A1 | 9/2009 | Nieuwkoop et al. | |
| 2009/0292194 A1 | 11/2009 | Libbus et al. | |
| 2010/0019721 A1 | 1/2010 | Reggiardo | |
| 2010/0049006 A1 | 2/2010 | Magar et al. | |
| 2010/0081913 A1 | 4/2010 | Cross et al. | |
| 2010/0317958 A1 | 12/2010 | Beck et al. | |
| 2010/0326703 A1 | 12/2010 | Gilad et al. | |
| 2011/0021937 A1 | 1/2011 | Hugh et al. | |
| 2011/0028822 A1 | 2/2011 | Beck | |
| 2011/0062241 A1 | 3/2011 | Beck | |
| 2011/0065476 A1 | 3/2011 | Hsiao et al. | |
| 2011/0270112 A1 * | 11/2011 | Manera | A61B 5/04288 |
| | | | 600/523 |
| 2011/0299713 A1 | 12/2011 | Moeller et al. | |
| 2012/0088999 A1 * | 4/2012 | Bishay | A61B 5/02438 |
| | | | 600/382 |
| 2014/0088398 A1 | 3/2014 | Beck | |
| 2014/0228665 A1 * | 8/2014 | Albert | A61B 5/0245 |
| | | | 600/384 |
| 2015/0073231 A1 | 3/2015 | Beck et al. | |
| 2015/0289814 A1 | 10/2015 | Magar et al. | |
| 2015/0374294 A1 | 12/2015 | Beck | |
| 2016/0015962 A1 | 1/2016 | Shokoueinejad et al. | |
| 2016/0022161 A1 * | 1/2016 | Khair | A61B 5/0496 |
| | | | 600/345 |
| 2017/0354376 A1 | 12/2017 | Beck | |

FOREIGN PATENT DOCUMENTS

| | | |
|---|---|---|
| WO | WO-0178594 A1 | 10/2001 |
| WO | WO-02089667 A1 | 11/2002 |
| WO | WO-03065926 A2 | 8/2003 |
| WO | WO-03065926 A3 | 6/2004 |
| WO | WO-2005094674 A1 | 10/2005 |
| WO | WO-2006061354 A1 | 6/2006 |
| WO | WO-2007060609 A2 | 5/2007 |
| WO | WO-2007060609 A3 | 10/2007 |
| WO | WO-2008006150 A1 | 1/2008 |
| WO | WO-2015127466 A2 | 11/2015 |
| WO | WO-2017165526 | 9/2017 |

OTHER PUBLICATIONS

EP15827134.6 Extended Search Report dated Feb. 22, 2018.
Notice of Allowance dated Nov. 23, 2016 for U.S. Appl. No. 14/805,389.
Office Action dated Aug. 3, 2016 for U.S. Appl. No. 14/805,389.
PCT/US2017/023601 International Search Report dated Jul. 7, 2017.
Wang, Y. et al., A low noise wearable wireless ECG system with body motion cancellation for long term homecare. IEEE 15th international conference on e-health networking, applications and services (healthcom 2013) 507-511.
International search report and written opinion dated Jan. 7, 2016 for PCT/US2015/042989.
International search report and written opinion dated May 28, 2009 for PCT Application No. US08/80695.
International search report and written opinion dated Jul. 20, 2009 for PCT Application No. US08/80659.
International search report and written opinion dated Sep. 29, 2008 for PCT Application No. US08/64800.
Notice of allowance dated Feb. 4, 2013 for U.S. Appl. No. 12/739,561.
Notice of allowance dated Mar. 14, 2014 for U.S. Appl. No. 12/601,373.
Notice of allowance dated Sep. 12, 2013 for U.S. Appl. No. 12/739,561.
Notice of allowance dated Oct. 7, 2015 for U.S. Appl. No. 12/739,553.
Notice of allowance dated Nov. 3, 2015 for U.S. Appl. No. 12/739,553.

(56) References Cited

OTHER PUBLICATIONS

Notice of allowance dated Dec. 19, 2013 for U.S. Appl. No. 12/601,373.
Office action dated Jan. 22, 2015 for U.S. Appl. No. 14/091,252.
Office action dated Feb. 27, 2015 for U.S. Appl. No. 14/244,760.
Office action dated Apr. 15, 2013 for U.S. Appl. No. 12/601,373.
Office action dated Jun. 26, 2012 for U.S. Appl. No. 12/739,561.
Office action dated Jul. 30, 2013 for U.S. Appl. No. 12/739,553.
Office action dated Aug. 31, 2012 for U.S. Appl. No. 12/601,373.
Office action dated Oct. 29, 2013 for U.S. Appl. No. 12/601,373.
Office action dated Nov. 21, 2012 for U.S. Appl. No. 12/739,553.
Office action dated Dec. 29, 2014 for U.S. Appl. No. 12/739,553.
Co-pending U.S. Appl. No. 14/997,401, filed Jan. 15, 2016.
EP17771062.1 Extended European Search Report dated Oct. 29, 2019.
"IPRP for PCT/US2017/023601 dated Sep. 25, 2018".
Romanowich, C.A., Voltage used to resuscitate a human heart, The Physics factbook, Jan. 1, 1999, XP055633665.
U.S. Appl. No. 14/244,760 Office Action dated Feb. 27, 2015.

\* cited by examiner

Mark four points in white, black, red and green color as shown in picture. All the marks should be 0.75' away from the edge and angle as given below 45 deg – Black
135 deg – Red
225 deg – Green
315 deg – White or blue

ECG PATCH AND METHODS OF USE

CROSS-REFERENCE

This application claims the benefit of U.S. Provisional Application No. 62/031,079, filed Jul. 30, 2014, and U.S. Provisional Application No. 62/186,277, filed Jun. 29, 2015, which applications are incorporated herein by reference.

BACKGROUND OF THE INVENTION

Monitoring physiological conditions of the human body has been an important component of health care. Although the monitoring can be performed periodically by health care professionals, increasingly the task is being handled by electronics that connect the patient to a computerized system for autonomous data storage, presentation and retrieval. Moreover, autonomous monitoring for collection of physiological data is becoming an important part of everyday life with the advent of the quantified-self movement.

Most sensors used in monitoring physically contact the body, requiring a method for connecting sensors to the rest of the electronic system. While simple sensors (e.g., a wrist monitor) have been used to collect simple data that tracks a person's physical activity or sleep patterns, cumbersome wires distributed throughout the body have traditionally been necessary to collect more meaningful physiological data.

SUMMARY OF THE INVENTION

Embodiments disclosed herein provide systems and methods for monitoring a user. A compact integrated patch may be used to collect physiological data. The patch may be wireless. The patch may be utilized in everyday life as well as in clinical environments. A quality of data acquired using the patch may depend on both a location of the patch on a user an orientation of the patch relative to a longitudinal axis of the user. The patch may comprise at most two instrumentation amplifiers. The patch may communicate with one or more external devices via wired and/or wireless connection. Data acquired by the patch and/or external devices may be interpreted and/or be utilized by healthcare professionals and/or computer algorithms (e.g., third party applications). Data acquired by the patch may be interpreted and be presented for viewing to healthcare professionals and/or ordinary users. The patch may communicate to a user (e.g., send an alert) based on the interpreted data.

Thus, in one aspect, an integrated patch is provided. The patch comprises: a base comprising two or more electrodes configured to gather information; a cover coupled to the base, wherein the cover comprises one or more indicators associated with a preferred placement or orientation of the patch; an electronic module in communication with the two or more electrodes, wherein the electronic module is housed between the base and the cover; and a radio in communication with the electronic module configured to wirelessly transmit or receive data.

In some embodiments, the base is circular and has a diameter equal to or less than 5 inches. In some embodiments, the base comprises four electrodes. In some embodiments, wherein each of the four electrodes correspond to at least a right arm (RA), left arm (LA), right leg (RL), and left leg (LL) electrode and are configured to gather information sufficient to generate at least three limb leads. In some embodiments, the four electrodes are arranged in a rectangular orientation. In some embodiments, the base further comprises a fifth electrode, wherein the fifth electrode is configured to reduce a noise of acquired signals. In some embodiments, the fifth electrode is located within at least 1.5 inches of the RL electrode. In some embodiments, the indicator is a symbol, marking, sign, or shape. In some embodiments, the indicator comprises an LED. In some embodiments, the indicator is associated with the preferred placement or orientation of the patch on a user. In some embodiments, the indicator responds to a correct placement of the patch on a user. In some embodiments, the preferred placement is near a center of a chest or near an upper right chest of a human being. In some embodiments, the patch is configured to communicate with one or more external devices via the radio. In some embodiments, the one or more external devices comprise cell phones, tablet, PDAs, or fitness trackers. In some embodiments, the radio comprises a triple mode hybrid radio able to communicate using Wi-Fi, Medical band, and ultra wideband bandwidths. In some embodiments, the base and the cover are made of the same material. In some embodiments, the base and the cover are made of silicone. In some embodiments, the patch further comprises a spacer configured to separate the base from the cover, wherein the spacer defines a space in which the electronic module is to be located in. In some embodiments, the spacer comprises an electrically insulating material. In some embodiments, the spacer prevents signal leakage between the electrodes. In some embodiments, the spacer comprises a shock absorbing material configured to absorb or redirect external forces. In some embodiments, the cover is removably coupled to the base. In some embodiments, the electronic module is removably coupled to the base. In some embodiments, the patch comprises one or more processors individually or collectively configured to analyze or process gathered information. In some embodiments, the patch comprises a visual, auditory, or haptic alert system configured to send an alert to a user based on gathered information.

In another aspect, an integrated patch is provided. The patch comprises: a base comprising two or more electrodes configured to measure a voltage; a cover coupled to the base; an electronic module in communication with the two or more electrodes, wherein the electronic module is housed between the base and the cover and comprises one or more instrumentation amplifiers configured to amplify a difference between voltages measured from two different electrodes; and a radio in communication with the electronic module configured to wirelessly transmit or receive data.

In some embodiments, the base is circular and has a diameter equal to or less than 5 inches. In some embodiments, the base comprises four electrodes. In some embodiments, each of the four electrodes correspond to at least a right arm (RA), left arm (LA), right leg (RL), and left leg (LL) electrode and are configured to gather information sufficient to generate at least three limb leads. In some embodiments, the four electrodes are arranged in a rectangular orientation. In some embodiments, the base further comprises a fifth electrode, wherein the fifth electrode is configured to reduce a noise of acquired signals. In some embodiments, the fifth electrode is located within at least 1.5 inches of the RL electrode. In some embodiments, the patch comprises at most two instrumentation amplifiers. In some embodiments, a first instrumentation amplifier amplifies a difference between voltage measured by the LA electrode and the LL electrode and the second instrumentation amplifier amplifies a difference between voltage measured by the RA electrode and the LL electrode. In some embodiments, a first instrumentation amplifier amplifies a difference between voltage measured by the LA electrode and the RA electrode and the second instrumentation amplifier amplifies a difference between voltage measured by the RA electrode and the LL electrode. In some embodiments, the patch is configured to communicate with one or more external devices via the radio. In some embodiments, the one or more external devices comprise cell phones, tablet, PDAs, or fitness trackers. In some embodiments, the radio comprises a triple mode hybrid radio able to communicate using Wi-Fi, Medical band, and ultra wideband bandwidths. In some embodiments, the base and the cover are made of the same material. In some embodiments, the base and the cover are made of silicone. In some embodiments, the patch further comprises a spacer configured to separate the base from the cover, wherein the spacer defines a space in which the electronic module is to be located in. In some embodiments, the spacer comprises an electrically insulating material. In some embodiments, the spacer prevents signal leakage between the electrodes. In some embodiments, the spacer comprises a shock absorbing material configured to absorb or redirect external forces. In some embodiments, the cover is removably coupled to the base. In some embodiments, the electronic module is removably coupled to the base. In some embodiments, the patch comprises one or more processors individually or collectively configured to analyze or process gathered information. In some embodiments, the patch comprises a visual, auditory, or haptic alert system configured to send an alert to a user based on gathered information.

In another aspect, an integrated patch is provided. The patch comprises: a base comprising two or more electrodes configured to gather information; a cover coupled to the base; one or more ports configured to communicate with one or more removably attachable electrodes; an electronic module in communication with the two or more electrodes, wherein the electronic module is housed between the base and the cover; and a radio in communication with the electronic module configured to wirelessly transmit or receive data.

In some embodiments, the base is circular and has a diameter equal to or less than 5 inches. In some embodiments, the base comprises four electrodes. In some embodiments, each of the four electrodes correspond to at least a right arm (RA), left arm (LA), right leg (RL), and left leg (LL) electrode and are configured to gather information sufficient to generate at least three limb leads. In some embodiments, the four electrodes are arranged in a rectangular orientation. In some embodiments, the base further comprises a fifth electrode, wherein the fifth electrode is configured to reduce a noise of acquired signals. In some embodiments, the fifth electrode is located within at least 1.5 inches of the RL electrode. In some embodiments, the one or more other electrodes are configured to gather information regarding precordial leads. In some embodiments, the patch is configured to communicate with one or more external devices via the radio. In some embodiments, the one or more external devices comprise cell phones, tablet, PDAs, or fitness trackers. In some embodiments, the radio comprises a triple mode hybrid radio able to communicate using Wi-Fi, Medical band, and ultra wideband bandwidths. In some embodiments, the base and the cover are made of the same material. In some embodiments, the base and the cover are made of silicone. In some embodiments, the patch further comprises a spacer configured to separate the base from the cover, wherein the spacer defines a space in which the electronic module is to be located in. In some embodiments, the spacer comprises an electrically insulating material. In some embodiments, the spacer prevents signal leakage between the electrodes. In some embodiments, the spacer comprises a shock absorbing material configured to absorb or redirect external forces. In some embodiments, the cover is removably coupled to the base. In some embodiments, the electronic module is removably coupled to the base. In some embodiments, the patch comprises one or more processors individually or collectively configured to analyze or process gathered information. In some embodiments, the patch comprises a visual, auditory, or haptic alert system configured to send an alert to a user based on gathered information.

In another aspect, an integrated patch is provided. The patch comprises: a base comprising two or more electrodes configured to gather information; a cover coupled to the base; one or more additional types of sensors configured to gather other information; an electronic module in communication with the two or more electrodes, wherein the electronic module is housed between the base and the cover; and a radio in communication with the electronic module configured to wirelessly transmit or receive data.

In some embodiments, the base is circular and has a diameter equal to or less than 5 inches. In some embodiments, the base comprises four electrodes. In some embodiments, each of the four electrodes correspond to at least a right arm (RA), left arm (LA), right leg (RL), and left leg (LL) electrode and are configured to gather information sufficient to generate at least three limb leads. In some embodiments, the four electrodes are arranged in a rectangular orientation. In some embodiments, the base further comprises a fifth electrode, wherein the fifth electrode is configured to reduce a noise of acquired signals. In some embodiments, the fifth electrode is located within at least 1.5 inches of the RL electrode. In some embodiments, the one or more additional types of sensors comprise sensors able to gather information regarding heart rate or respiration of a user. In some embodiments, the one or more additional types of sensors comprise sensors able to gather information regarding ambulatory data of a user. In some embodiments, the one or more additional types of sensors comprise sensors able to gather information regarding hydration, temperature, SpO2, or blood pressure of a user. In some embodiments, the one or more additional types of sensors comprise sensors able to gather information regarding acceleration, audio, vision, or pressure of an environment around the patch. In some embodiments, the patch is configured to communicate with one or more external devices via the radio. In some embodiments, the one or more external devices comprise cell phones, tablet, PDAs, or fitness trackers. In some embodiments, the radio comprises a triple mode hybrid radio able to communicate using Wi-Fi, Medical band, and ultra wideband bandwidths. In some embodiments, the base and the cover are made of the same material. In some embodiments, the base and the cover are made of silicone. In some embodiments, the patch further comprises a spacer configured to separate the base from the cover, wherein the spacer defines a space in which the electronic module is to be located in. In some embodiments, the spacer comprises an electrically insulating material. In some embodiments, the spacer prevents signal leakage between the electrodes. In some embodiments, the spacer comprises a shock absorbing material configured to absorb or redirect external forces. In some embodiments, the cover is removably coupled to the base. In some embodiments, the electronic module is removably coupled to the base. In some embodiments, the patch comprises one or more processors individually or collectively configured to analyze or process gathered information. In some embodiments, the patch comprises a visual, auditory, or haptic alert system configured to send an alert to a user based on gathered information.

In another aspect, a method of collecting physiological data is provided. The method comprises: providing an integrated patch comprising: a base comprising two or more electrodes configured to gather information; a cover coupled to the base, wherein the cover comprises one or more indicators associated with a preferred placement or orientation of the patch; a radio configured to wirelessly transmit or receive data; and an electronic module comprising an ASIC housed between the base and the cover; and placing the patch on a user based on the one or more indicators; and collecting information from the patch.

In another aspect, a method of amplifying a differential signal between two input signal voltages is provided. The method comprises: providing a patch comprising: a base comprising two or more electrodes configured to measure a voltage; a cover coupled to the base; a radio configured to wirelessly transmit or receive data; and an electronic module comprising: an ASIC housed between the base and the cover; and one or more instrument amplifiers configured to amplify a difference between voltages measured from two different electrodes; measuring a voltage from the two or more electrodes; and amplifying a difference between the measured voltages.

In another aspect, a system for acquiring physiological signals is provided. The system comprises: a wireless integrated patch; an instruction regarding a recommended placement and orientation of the patch.

In some embodiments, the recommended placement comprises at least two different locations on the human body and wherein an orientation of the patch is different depending on the different locations.

In another aspect, a method of placing a wireless integrated patch on a user is provided. The method comprises: matching a placement and orientation of the patch to a provided figure; and placing the patch according to the provided figure.

In another aspect, a method of collecting physiological data is provided. The method comprises: providing any of the aforementioned integrated patch; placing the patch on a user at a preferred location or in a preferred orientation; and collecting information from the patch.

In some embodiments, the method further comprises sending the collected information to an external device for processing of the collected information. In some embodiments, the method further comprises sending an alert to the user based on the processed information.

In another aspect, an integrated wireless patch is presented. The patch comprises: a base, wherein the base comprises at least four electrodes; a cover; an electronic module housed between the base and the cover, wherein the electronic module comprises at most two instrumentation amplifiers, and wherein the patch is capable of generating three limb leads.

In another aspect, an integrated wireless patch is presented. The patch comprises a base, wherein the base is at most 4 inches in diameter and comprises four electrodes arranged in a square configuration, wherein the four electrodes correspond to.

In another aspect, a method of placing an integrated wireless patch is presented. The method comprises placing a patch comprising two or more electrodes.

It shall be understood that different aspects of the invention can be appreciated individually, collectively, or in combination with each other. Various aspects of the invention described herein may be applied to any of the particular applications set forth below. Other objects and features of the present invention will become apparent by a review of the specification, claims, and appended figures.

INCORPORATION BY REFERENCE

All publications, patents, and patent applications mentioned in this specification are herein incorporated by reference to the same extent as if each individual publication, patent, or patent application was specifically and individually indicated to be incorporated by reference in their entirety.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Provided herein are patches comprising a base, a cover, and an electronic module located therebetween. The patch may be used for acquisition of physiological data. For example, the patch may be used for acquisition of data relating to electrocardiography (ECG).

Figure 1:
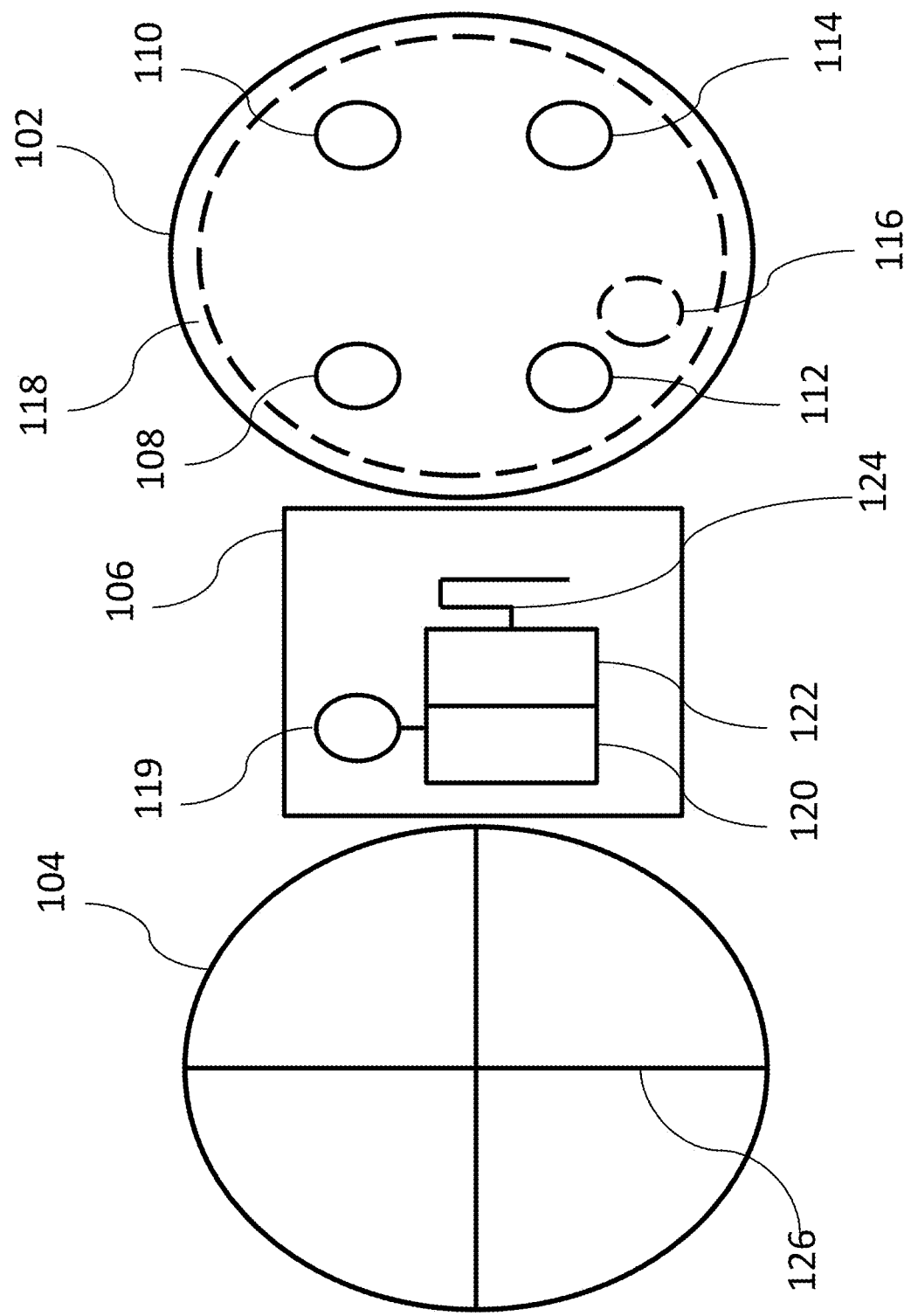
FIG. 1 illustrates a dissembled patch, in accordance with embodiments.

FIG. 1 illustrates components of a patch, in accordance with embodiments. The patch may comprise at least a base 102, a cover 104, and an electronic module 106. The electronic module may be located between the base and the cover (e.g., sandwiched between the base and the cover).

The base 102 may be configured to come into contact with a surface (e.g., skin) of a user. While a circular base is illustrated in FIG. 1, the base may be of any shape, including circular, semi-circular, oval, rectangular, polygonal, or of any arbitrary shape. The base may be made of any material including synthetic polymers such as thermoplastics, thermosets, elastomers, and synthetic fibers. The base may be inert. The base may be flexible or rigid. The base may be stretchable or non-stretchable. The base may be compressible or non-compressible. In some instances, the base may be made of a biocompatible material, such as silicone. In some instances, the base may be a made of a shape conforming material that conforms to a shape of the user. The base may be of any size. In some instances, the base may be less than about 2 inches, 2.5 inches, 3 inches, 3.5 inches, 4 inches, 4.5 inches, or 5 inches, 5.5 inches, 6 inches, 7 inches, or 8 inches in length or diameter. In some instances, the base may be greater than about 2 inches, 2.5 inches, 3 inches, 3.5 inches, 4 inches, 4.5 inches, 5 inches, 5.5 inches, 6 inches, 7 inches, or 8 inches in length or diameter. In some instances, the base may be about 3.5 inches in length or diameter.

The base may comprise four electrodes 108, 110, 112, 114. In some instances, the base may comprise one, two, three, four, five, six or more electrodes. In some instances, the base may comprise no more than one, two, three, four, five, or six electrodes. The electrodes may be integrated into the base. The electrodes may be separate components from the base that are releasably or permanently coupled to the base. As referred to herein, a base comprising electrodes may refer to a base to which electrodes are coupled to. For example, the four electrodes shown in FIG. 1 may be electrodes shown through openings or holes on the base. Each of the electrodes may be located equal to about or greater than 0.25 inches, 0.5 inches, 0.75 inches, 1 inch, 1.25 inches, 1.5 inches, 1.75 inches, or 2 inches away from the edge of the base. Each of the electrodes may be located equal to about or less than 0.25 inches, 0.5 inches, 0.75 inches, 1 inch, 1.25 inches, 1.5 inches, 1.75 inches, or 2 inches away from the edge of the base.

The electrodes may be positioned relative to one another. For example, the electrodes may be located equal to or less than about 0.25 inches, 0.5 inches, 0.75 inches, 1 inch, 1.25 inches, 1.5 inches, 2 inches, 2.25 inches, 2.5 inches, 2.75 inches, or 3 inches from one another. For example, the electrodes may be located equal to or more than about 0.25 inches, 0.5 inches, 0.75 inches, 1 inch, 1.25 inches, 1.5 inches, 2 inches, 2.25 inches, 2.5 inches, 2.75 inches, or 3 inches from one another. For example, the electrodes may be located between about 0.25 inches, 0.5 inches, 0.75 inches, 1 inch, 1.25 inches, 1.5 inches, 2 inches, 2.25 inches, 2.5 inches, 2.75 inches, or 3 inches from one another. The electrodes may be spaced equidistant from one another. The electrodes may be radially spaced equidistant from one another. For example, for a base having N electrodes, the electrodes may be angularly spaced 360/N degrees from each other. The electrodes may be angularly spaced 45°, 60°, 90°, 120°, or 180° from one another measured from a center of the base. In some instances, the electrodes may be arranged in a circular pattern or rectangular pattern. The electrodes may be radially symmetric about a line that bisects a center of the base. Each of the electrodes may gather information (e.g., measure a voltage) from the location where it is placed. The information may be sent to an electronic module, e.g., through conductive traces as further described below.

For a base comprising four electrodes, each of the electrodes 108, 110, 112, 114 may correspond to limb electrodes that are placed on a user in conventional ECG. For example, electrode 108 may correspond to a right arm (RA) electrode, electrode 110 may correspond to a left arm (LA) electrode, electrode 112 may correspond to a right leg (RL) electrode, and electrode 114 may correspond to a left leg (LL) electrode as used in a conventional ECG monitor. Three limb leads (Lead I, Lead II, and Lead III) and three augmented limb leads (aVR, aVL, and aVF) may be calculated according to conventional calculations using data (e.g., voltage) acquired from the RA, LA, LL, and RL electrodes. In some instances, the base may comprise a fifth electrode 116. The fifth electrode may be utilized to further reduce noise of acquired signals (e.g., used as a second RL electrode). The fifth electrode may be located about or within at least 0.25 inches, 0.5 inches, 0.75 inches, 1 inch, 1.25 inches, or 1.5 inches of the RL electrode 114.

The base may further comprise cutouts. The cutouts may define a space through which the electrodes may contact the user. The cutouts may closely trace or define a shape of the electrodes that were described herein. In some instances, the cutouts can be surrounded by spiral cutouts. The spiral cutouts may provide flexibility between the base and the skin of the user and may serve to reduce strain between the base and the skin surface. In some embodiments, the cutouts of the base may comprise adhesives that surround the cutouts. The adhesives may be configured to couple the patch to a skin of the user. The cutouts may further be filled with a gel (e.g., electrode gel) that conducts an electrical signal from a surface of the user. The electrode gel may be used in conjunction with the adhesive washers and the cutouts to facilitate communication between the surface of the user and the electrodes. In some instances, the base (e.g., and/or cover or spacer, further described herein) may comprise a removable layer. The removable layer may provide a protective layer against the surrounding environment (e.g., dust, light, water, etc) during storage and/or prior to utilization of the patch. The removable layer may be configured to be peeled off by a user prior to usage of the patch. For further description regarding, cutouts, spiral cutouts, adhesives, and gels, please refer to U.S. Pat. Nos. 8,628,020, 8,718,742, and U.S. Publication No. 2011/0028822 which are hereby incorporated by reference in their entirety.

Figure 18:
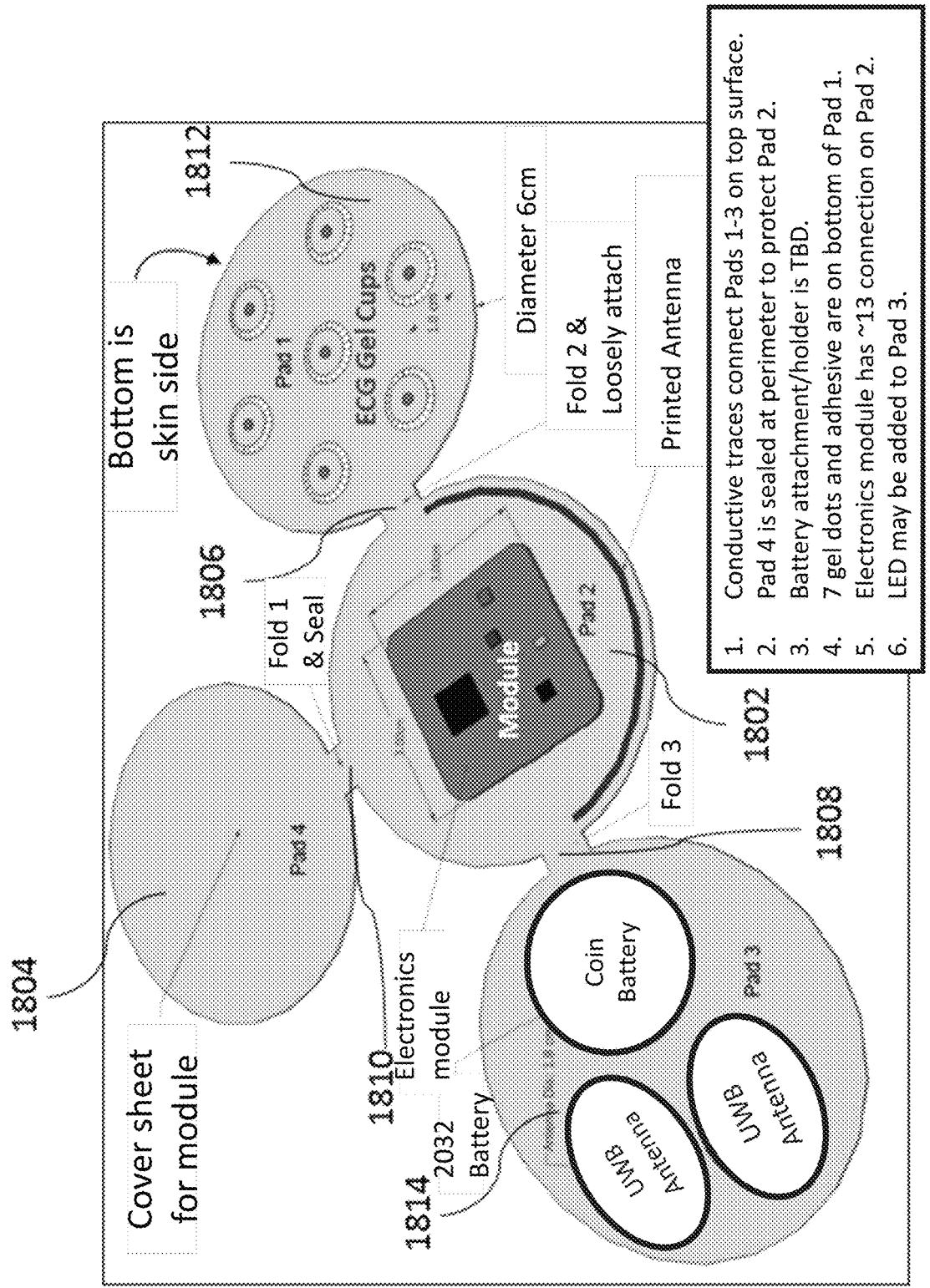
FIG. 18 illustrates a foldable patch design, in accordance with embodiments.
Figure 19:
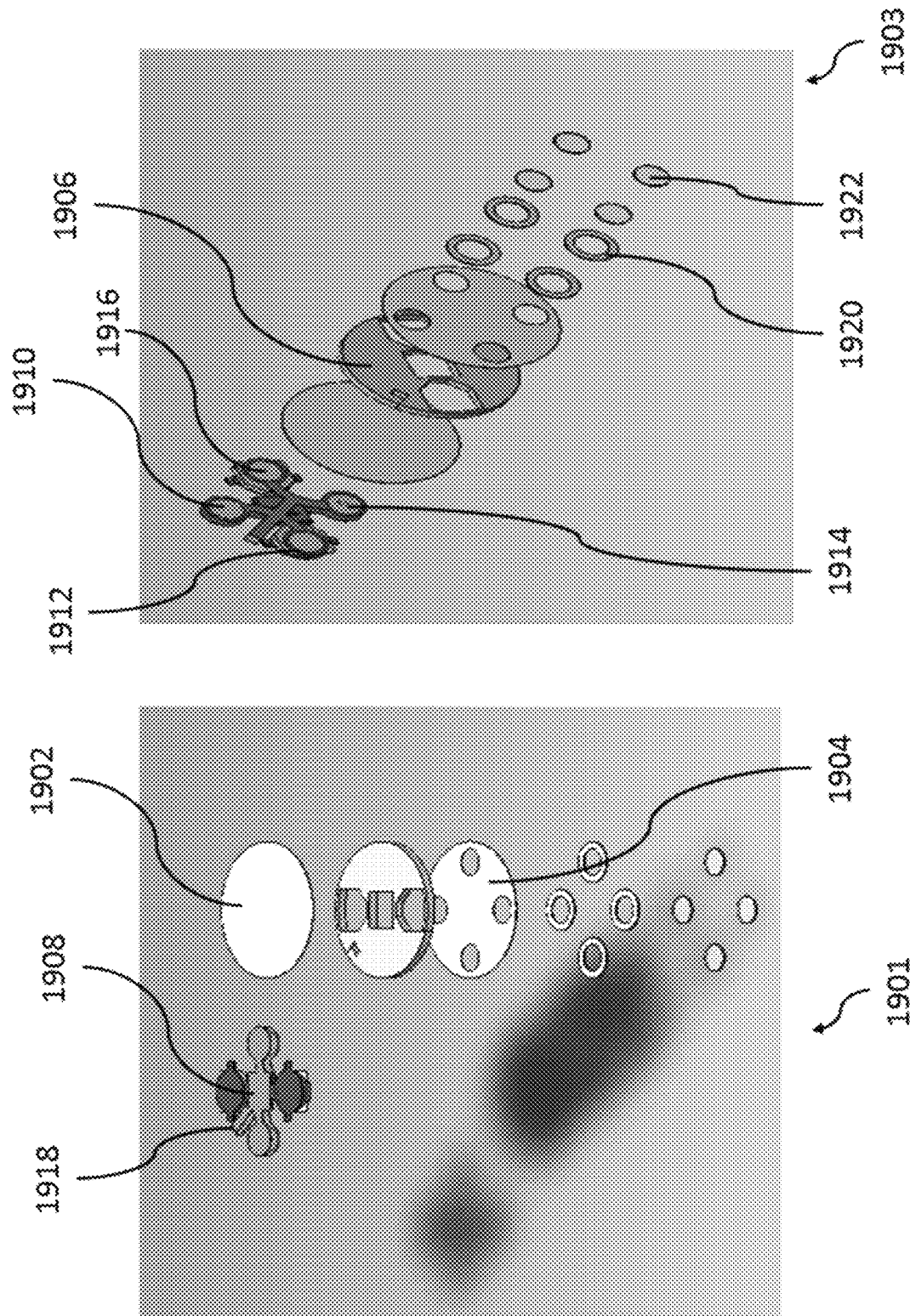
FIG. 19 illustrates two different perspectives of a blown up view of a patch design, in accordance with embodiments.

In some instances, the patch may comprise a spacer. The spacer may be made of any material including synthetic polymers such as thermoplastics, thermosets, elastomers, and synthetic fibers. The spacer may be inert. The spacer may be flexible or rigid. The spacer may be stretchable or non-stretchable. The spacer may be compressible or non-compressible. The spacer may be coupled to the base and/or cover. The spacer may be configured to couple the base to the cover. In some instances, the spacer may be configured to separate the base from the cover. The spacer may define a space in which an electronic module is to be located within. In some instances, the spacer may comprise a mid-layer that can house the electronic module. For example, FIG. 19 illustrates a spacer 1906 that may house the electronic module 1908. In some instances, the spacer may comprise a fold 1806, 1808, or 1810 connecting the base and the cover which may be folded over, as illustrated in FIG. 18. In some instances, the spacer may comprise a hollow cylindrical column 118 configured to provide an empty space between the base and the cover in which the electronic module may be placed, as illustrated in FIG. 1. The spacer may be coupled to the base and/or cover removably (e.g., with adhesives, lock on mechanism, etc) or permanently. In some instances, the spacer may be coupled to the base permanently and the spacer may be coupled to the cover removably, or vice versa. In some instances, the spacer may be integrated into the base and/or cover (e.g., as a single mold). The spacer may comprise an electrically insulating material. In some instances, the spacer may prevent signal leakage between the electrodes. The spacer may comprise a shock absorbing material. The spacer may add a bit of thickness to keep the electronic module from sticking out too far (e.g., into the cover). The spacer may provide protection to the electronic module. The spacer may absorb or redirect external forces such that the electronic module is protected from external forces. In some instances, the spacer may be made of the same material as the base and/or the cover. For example, the spacer may be made of silicone.

The electronic module 106 may be coupled to the base. The electronic module may be in communication with one or more electrodes (e.g., electrodes 108, 110, 112, 114, or 116). In some instances, the electronic module may be in communication with each of the electrodes of the patch. In some instances, the electronic module may be directly coupled to the base. For example, the electronic module may be mechanically or chemically fixed on top of the base. In some instances, the electronic module may be housed within the mid-layer (e.g., spacer) which is coupled to the base. The electronic module may comprise a multi-chip module or ASIC to integrate most of the needed functions into a single module. The ASIC can be a single chip device. In some embodiments, additional components can be added to the ASIC as needed. For example, the electronic module may comprise additional components such as sensors (e.g., accelerometers), microphones, batteries 119, sensor interfaces 120, radios 122, antennas 124, memory, etc. Alternatively or in addition, the aforementioned additional components may be located elsewhere on the patch and the electronic module may be in communication with the additional components.

The radio 122 may enable the patch to communicate with other devices through a wireless link. The radio may be configured to wirelessly transmit and/or receive data. The radio may be configured to wirelessly transmit data to external devices and/or receive data from the external devices. The radio may be a single-mode, dual-mode, triple-mode, or quad-mode radio. The radio may utilize any known bandwidth, e.g., narrowband, wideband, ultra wideband, broadband, etc. The radio may communicate through Wi-Fi, Bluetooth, wireless usb, etc. In some instances, the radio may be a triple-mode hybrid radio. The triple-mode hybrid radio may utilize Wi-Fi, Medical band, and/or ultra wideband bandwidths. The triple-mode hybrid radio may seamlessly transition between the three modes to maintain link integrity. The triple-mode hybrid radio may select a lowest power option when more than one option is available. Alternatively, the radio may be a single-mode or dual-mode radio. For example, the single-mode radio may utilize Wi-Fi. For example, the single-mode radio may utilize Medical band bandwidths. For example, the single-mode radio may utilize ultra wideband bandwidths.

The cover 104 may be configured to be coupled to the base. In some instances, the cover may be coupled to the spacer. In some instances, the cover may be coupled to the base via the spacer. The cover may be made of any material including synthetic polymers such as thermoplastics, thermosets, elastomers, and synthetic fibers. The cover may be inert. The cover may be flexible or rigid. The cover may be stretchable or non-stretchable. The cover may be compressible or non-compressible. The cover, together with the base (e.g., and spacer) may provide an enclosure or a housing for the electronic module. The housing may provide protection and/or isolation to the electronic module from the surrounding environment, e.g., water, dust, light, air, etc. In some instances, the housing may be waterproof. While a circular cover is illustrated in FIG. 1, the cover may be of any shape, including circular, semi-circular, rectangular, polygonal, or of any arbitrary shape. In some instances, the base may be of the same or similar shape as the base. The cover may be made of any material. In some instances, the cover may be made of a biocompatible material, such as silicone. In some instances, the base may be a made of a shape conforming material that conforms to a shape of the electronic module. In some instances, the cover may be made of the same material as the base. In some instances, the base and cover may be made of different materials.

The cover may be of any size. In some instances, the cover may be less than about 2 inches, 2.5 inches, 3 inches, 3.5 inches, 4 inches, 4.5 inches, 5 inches, 5.5 inches, 6 inches, 7 inches, or 8 inches in length or diameter. In some instances, the cover may be greater than about 2 inches, 2.5 inches, 3 inches, 3.5 inches, 4 inches, 4.5 inches, 5 inches, 5.5 inches, 6 inches, 7 inches, or 8 inches in length or diameter. In some instances, the cover may be about 3.5 inches in length or diameter. In some instances, the cover may be of the same size as the base. In some instances, the cover may be about 5%, 10%, 15%, or 20% larger than the base. In some instances, both the base and cover may be made of silicone. In some instances, the base, cover, and spacer may be made of silicone. For example, the base, cover, and spacer may be made from medical or food grade silicone.

The cover may comprise an input/output (I/O) used to communicate information from the patch to a user or a healthcare professional. Input/outputs include, but are not limited to, light emitting diodes (LEDs), switches, or any other suitable indicator or actuator. In some instances, the cover may comprise a display. For example, the patch may comprise a display screen (e.g., LED or LCD screen). The display screen may be a touch screen. The display may display the various monitored physiological parameters. In some instances, devices coupled to the patch (e.g., physical monitoring device, mobile devices, computer, tablet, etc) may display the various monitored physiological parameters.

The cover may be configured to convey information to a user of the patch or to a healthcare professional. The cover may comprise one or more indicators 126. The indicators may be markings such as a sign, symbol, or figure (e.g., X sign or + sign). The indicators may be a color. For example, a color may be used to indicate a functionality or capability of the patch. In some instances, the markings may signify a recommended orientation of the patch or a placement of the patch with respect to the user. In some instances, the one or more indicators may comprise the input/output previously mentioned herein. For example, the cover may comprise an LED. The LED may respond to (e.g., light up) being placed on a user in a correct orientation or on a correct position on the user. A correct orientation and/or placement may be important for obtaining meaningful information from the patch, as further described below.

The patch may be utilized in acquiring various data. For example, the patch may acquire ECG data, e.g., 6-wave ECG data. The patch may acquire heart rate and respiration data. The patch may acquire data regarding acceleration, hydration, temperature, SpO2, and/or blood pressure. The patch may acquire data related to ambulatory data. The patch may acquire data regarding a motion and/or location of a user. The patch may acquire data related to auditory, visual, or barometric data of the user or an environment around the user. In some instances, patch may be used for lead off detection.

In some instances, a single patch may be provided for acquiring the various aforementioned data. In some instances, the patch may provide a modular platform on which additional sensor interfaces may be added or subtracted on depending on a user's need. In some instances, different patches with different functionalities and sensor interfaces may be provided. In some instances, the patch may comprise swappable parts (e.g., electronic modules) which may be swapped out depending on a user's needs. In some instances, components of the patch may be supplemented and/or upgraded for additional capabilities (e.g., additional sensors). The patch as described herein may comprise additional free space in which additional sensor interfaces may be added or taken away for acquisition of additional data. The patch as described herein may comprise modular components (e.g., sensors, swappable parts) that may be swapped in and out of the patch to give the patch different functionalities depending on a user's needs.

Figure 2:
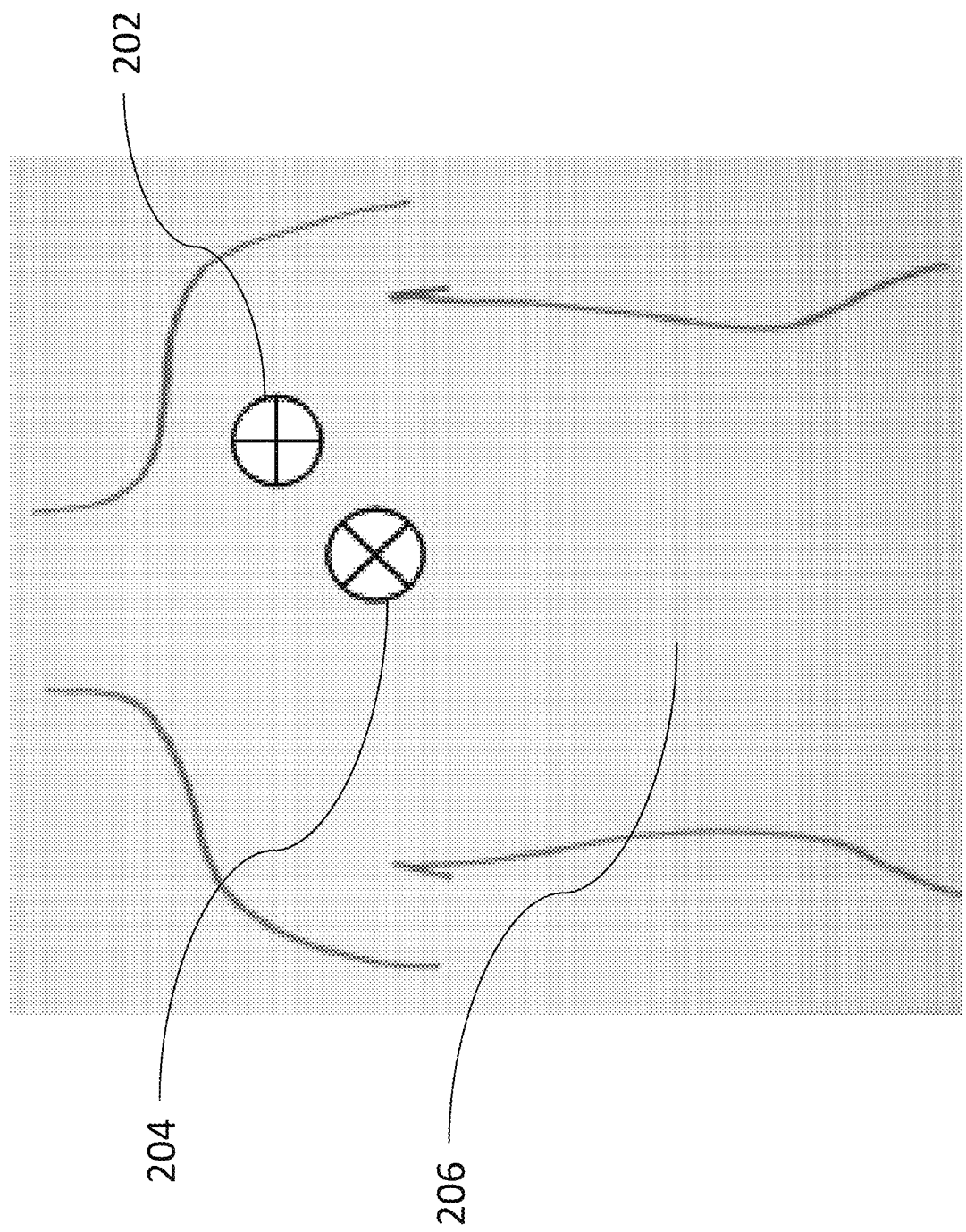
FIG. 2 illustrates a relative placement and orientation of the patch, in accordance with embodiments.

FIG. 2 illustrates an orientation and placement of patch that generates meaningful, or high quality data, in accordance with embodiments. High quality data as used herein may refer to precise, accurate, interpretable, and/or reproducible data. A first patch 202 and a second patch 204 may both illustrate the patch described in FIG. 1 placed at two different locations on a human body. The first patch shows a marking imitating an addition sign on the cover while the second patch shows a marking imitating a multiplication sign on the cover. The second patch may show a rotated first patch that is placed on a different location on the user 206. A single patch may be sufficient to collect high quality data.

A placement of the patch on the human body may be of importance for obtaining a high quality data. For example, high quality data may be obtained when the patch is placed near the upper left chest (e.g., location of patch 202) or at a center of the chest (e.g., location of patch 204). A patch placed near a center of the chest may be centered over the sternum. A patch placed near a center of the chest may be centered over the sternum and no lower than the xiphoid process.

An orientation of the patch may be of importance for obtaining high quality data. For example, when the patch is placed near the upper left chest, electrodes arranged in a normal orientation (e.g., relative to a longitudinal axis of the user) may enable acquisition of high quality data. A normal orientation as used herein may refer to an arrangement of electrodes as illustrated in FIG. 1. For example, a normal orientation of electrodes may be arranged in a rectangular shape relative to a longitudinal axis of the user. Electrodes arranged in a normal orientation may have a virtual line going through a LA electrode and a RA electrode be substantially perpendicular to a longitudinal axis of the user. Electrodes arranged in a normal orientation may have a virtual line going through a LL electrode and a RL electrode be substantially perpendicular to a longitudinal axis of the user. Electrodes arranged in a normal orientation may have a virtual line going through a LA and a LL electrode be substantially parallel to a longitudinal axis of the user. Electrodes arranged in a normal orientation may have a virtual line going through a RA and a RL electrode be substantially parallel to a longitudinal axis of the user. The configuration of electrodes as illustrated in FIG. 1 (e.g., relative to a longitudinal axis of the user) may enable acquisition of high quality data when the patch is placed near the upper left chest. The configuration of electrodes as illustrated in FIG. 1 may enable acquisition of high quality data when the patch is placed near a center of the chest.

In some instances, a different orientation of the patch may be preferred relative to a longitudinal axis of the user. For example, electrodes arranged in a tilted orientation (e.g., relative to a longitudinal axis of the user) may enable acquisition of high quality data. A tilted orientation as used herein may refer to an arrangement of electrodes that is rotated about 15°, 30°, 45°, 60°, 75°, 90°, 120°, 150°, 180° or more clockwise from the normal orientation. A tilted orientation as used herein may refer to an arrangement of electrodes that is rotated about 15°, 30°, 45°, 60°, 75°, 90°, 120°, 150°, 180° or less clockwise from the normal orientation. A tilted orientation as used herein may refer to an arrangement of electrodes that is rotated about 15°, 30°, 45°, 60°, 75°, 90°, 120°, 150°, 180° or more counterclockwise from the normal orientation. A tilted orientation as used herein may refer to an arrangement of electrodes that is rotated about 15°, 30°, 45°, 60°, 75°, 90°, 120°, 150°, 180° or less counterclockwise from the normal orientation. A tilted orientation as used herein may refer to an arrangement of electrodes that is rotated 15°, 30°, 45°, 60°, 75°, 90°, 120°, 150°, or 180° clockwise or counterclockwise from the normal orientation. In some instances, a tilted orientation of electrodes may be arranged in a diamond shape relative to a longitudinal axis of the user. Electrodes arranged in a tilted orientation may have a virtual line going through a LA electrode and a RL electrode be substantially parallel to a longitudinal axis of the user. Electrodes arranged in a tilted orientation may have a virtual line going through a LL and RA electrode be substantially perpendicular to a longitudinal axis of the user. Electrodes arranged in a tilted orientation may have a virtual line going through a LL electrode and a RA electrode be substantially parallel to a longitudinal axis of the user. Electrodes arranged in a tilted orientation may have a virtual line going through a LA and RL electrode be substantially perpendicular to a longitudinal axis of the user.

In some instances, a kit for obtaining physiological data may be provided. The kit may comprise a patch (e.g., as previously described herein) and instructions regarding a relative placement and orientation of the patch. The instructions may provide a recommended placement and/or orientation of the patch (e.g., as illustrated in FIG. 2). In some instances, a kit for obtaining physiological data may comprise a patch and instructions regarding at least two different positions and orientations of the patch. The orientation of the patch may depend on a recommended placement (e.g., position) of the patch.

Figure 3:
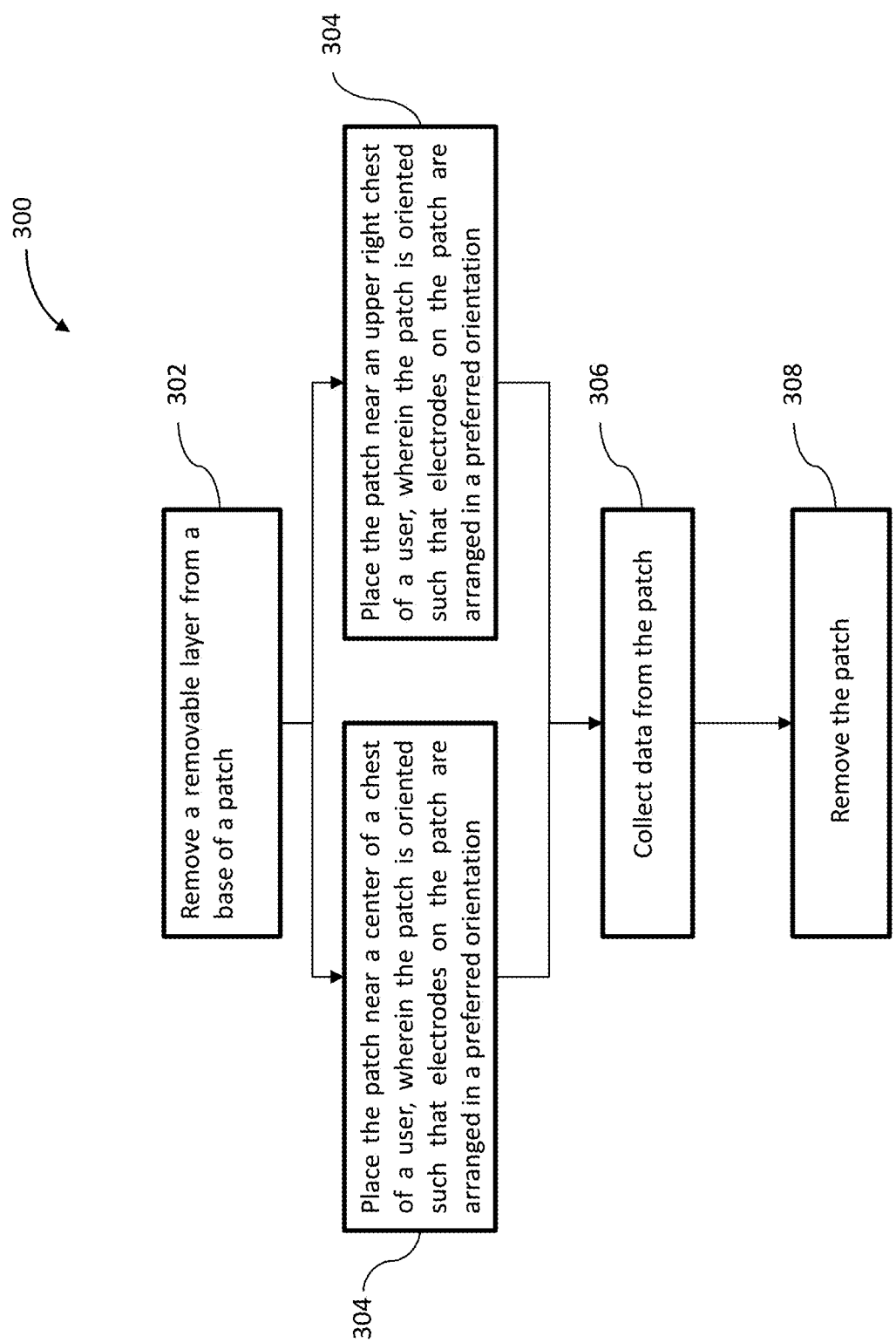
FIG. 3 illustrates a method of collecting physiological data, in accordance with embodiments.

FIG. 3 illustrates a method of collecting physiological information, in accordance with embodiments. In step 302, a removable layer is removed from a base of a patch. The removable layer may be as previously described herein (e.g., configured to provide protection from environmental factors prior to usage). The removable layer may be removed by a user of the patch. The removable layer may comprise a tab. The tab may be configured to aid a user in easily removing the removable layer. In some instances, removable layer may comprise markings to indicate a desired placement and/or orientation of the patch. In some instances, the tab may be configured to indicate a desired placement and/or orientation of the patch.

In step 304, the patch is placed near a center of a chest of a user, wherein the patch is oriented such that electrodes on the patch are arranged in a preferred orientation relative to a longitudinal axis of the user, as previously described herein (e.g., in a normal orientation). Alternatively, the patch is placed near an upper right chest of a user, wherein the patch is oriented such that electrodes on the patch are arranged in a preferred orientation relative to a longitudinal axis of the user, as previously described herein (e.g., in a normal orientation).

In step 306, data is collected from the patch. The data may comprise physiological data regarding the user. The data may comprise ECG data. The data may comprise 6-wave ECG data. The data may comprise heart rate and respiration data. The data may comprise acceleration, hydration, temperature, SpO2, and blood pressure. The data may comprise ambulatory data. The data may comprise data regarding a motion, location of the user. The data may comprise auditory, visual, or barometric data of the user or an environment around the user. In some instances, patch may be used for lead off detection. A lead-off detection may detect whether a lead that is supposed to be hooked up is not properly connected (e.g., to a user, etc). To detect lead-off, an impedance between each of the differential-sensing electrodes and a lead-off electrode may be monitored by the patch. In some instances, this impedance measurement may additionally provide an input for measurements of respiration rate.

In step 308, the patch is removed. In some instances, the whole patch may be removed and discarded. In some instances, part of the patch may be removed and discarded. For example, a base of the patch may be removed and discarded while an electronic module of the patch may be reused.

Figure 4:
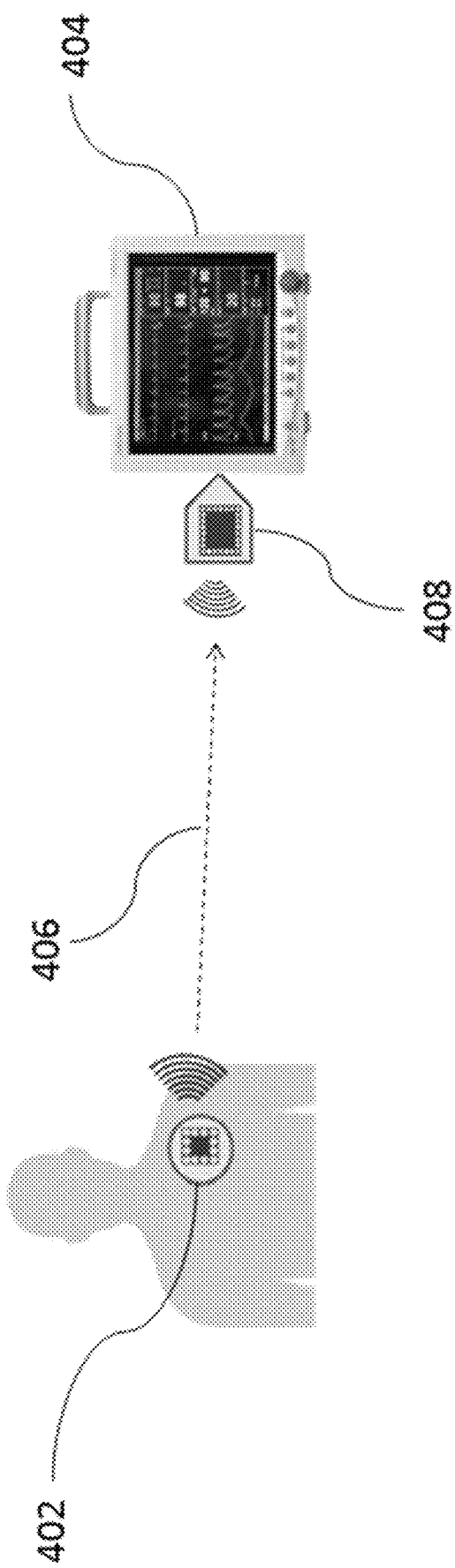
FIG. 4 illustrates patch in communication with clinical monitor via wireless link, in accordance with embodiments.

The patch may communicate with a clinical monitor (e.g., conventional ECG monitor) and/or any other device for reading and/or interpreting ECG related data. The patch may communicate with the clinical monitor through a wired connection and/or wireless connection (e.g., radio, wifi, Bluetooth, etc). FIG. 4 illustrates patch 402 in communication with clinical monitor 404 via wireless link 406. For example, two wireless devices may be used. The patch (e.g., electronic module) may comprise a wireless communication device (e.g., radio), as previously described herein, and the clinical monitor may be fit (e.g., retrofit) with an adaptor 408. The radio may be as previously described herein (e.g., a triple-mode hybrid radio).

The adaptor may be configured to receive data signals (e.g., via wireless link) from one or more patches and output data to the clinical monitor which can read and/or interpret the data. In some instances, the radio may send signals one way to the adaptor, and the adaptor may be configured to receive the signals, but not communicate back to the patch (e.g., the radio on the patch). In some instances, a communication scheme between the patch (e.g., the radio on the patch) and the adaptor may be two ways such that the adaptor may receive signals from the patch and send signals back to the patch. For further description regarding wireless communication schemes, please refer to U.S. Pat. Nos. 8,926,509 and 9,019,934 which are hereby incorporated by reference in their entirety.

Figure 5:
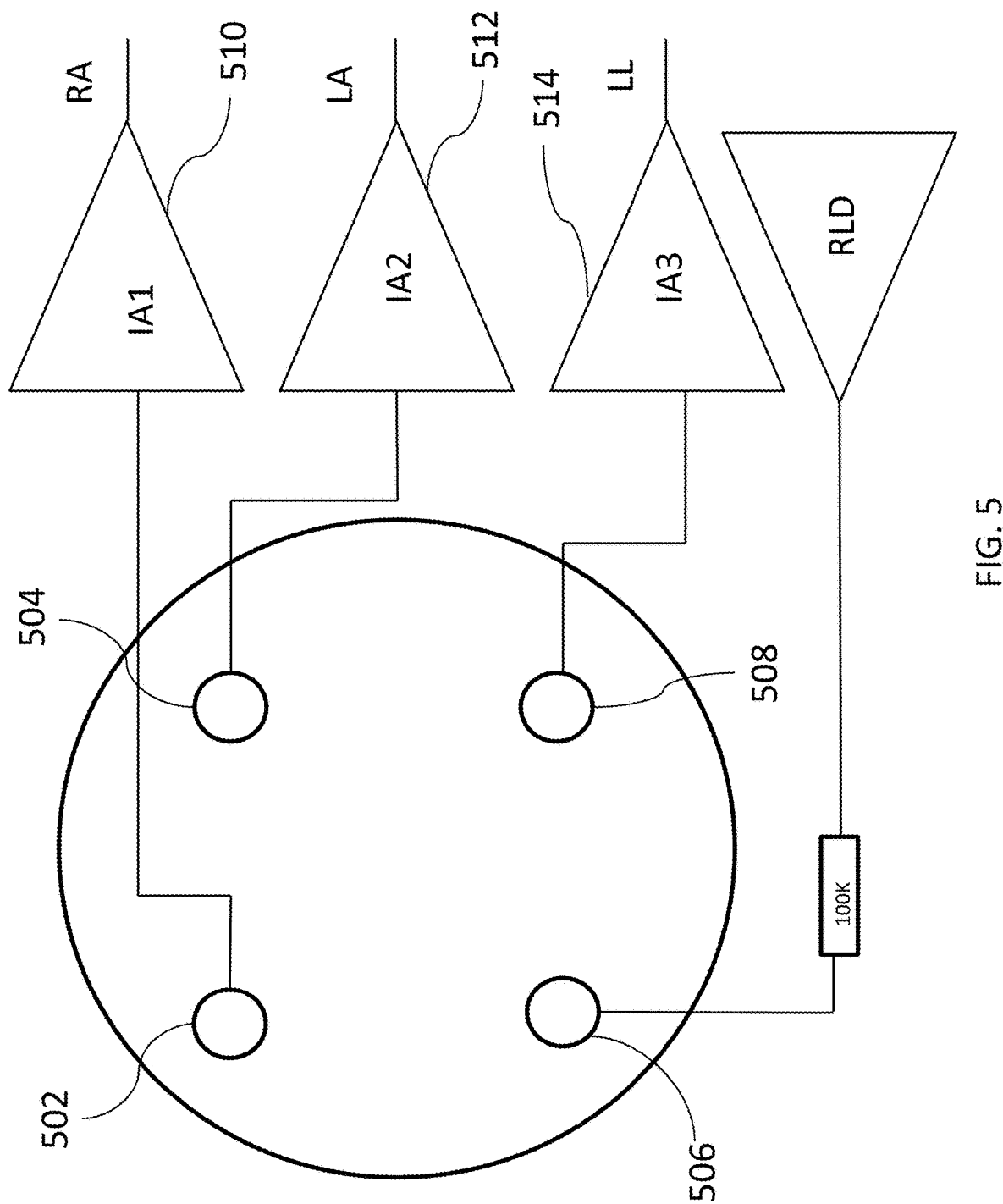
FIG. 5 illustrates a single ended amplification of signal from electrodes.

Instrumentation amplifiers (IA) may be used to amplify signals (e.g., voltage signals). In some instances, IAs may amplify an input signal (e.g., amplify a single ended input). The IAs may be integrated into the patch. Alternatively, the IAs may be integrated into the clinical monitors. FIG. 5 illustrates a single ended amplification of signal from electrodes. Electrode 502, 504, 506, and 508 may correspond each to the RA, LA, RL, and LL electrodes as designated in a conventional ECG. A wireless patch may accomplish lead-off detection for RA, LA, and LL, as previously described herein. A wireless patch may acquire the RA, LA, and LL signals and amplify the signals using three different IAs 510, 512, 514 as illustrated. The signals may be sent via wireless link as previously discussed herein to the adaptor. The signals may be further processed to generate the lead signals. Acquisition of RA, LA, LL signals in a single ended manner and reproducing the same at the adaptor (e.g., via wireless link) may have shortcomings. In some instances, due to being a single ended signal acquisition, the power supply pick up may not be rejected, and a noise of the signal may be high. Additionally, the number of IAs that are necessary may necessarily correspond to a number of electrode signals being measured, which may lead to a high data rate burden on the wireless link.

Figure 6:
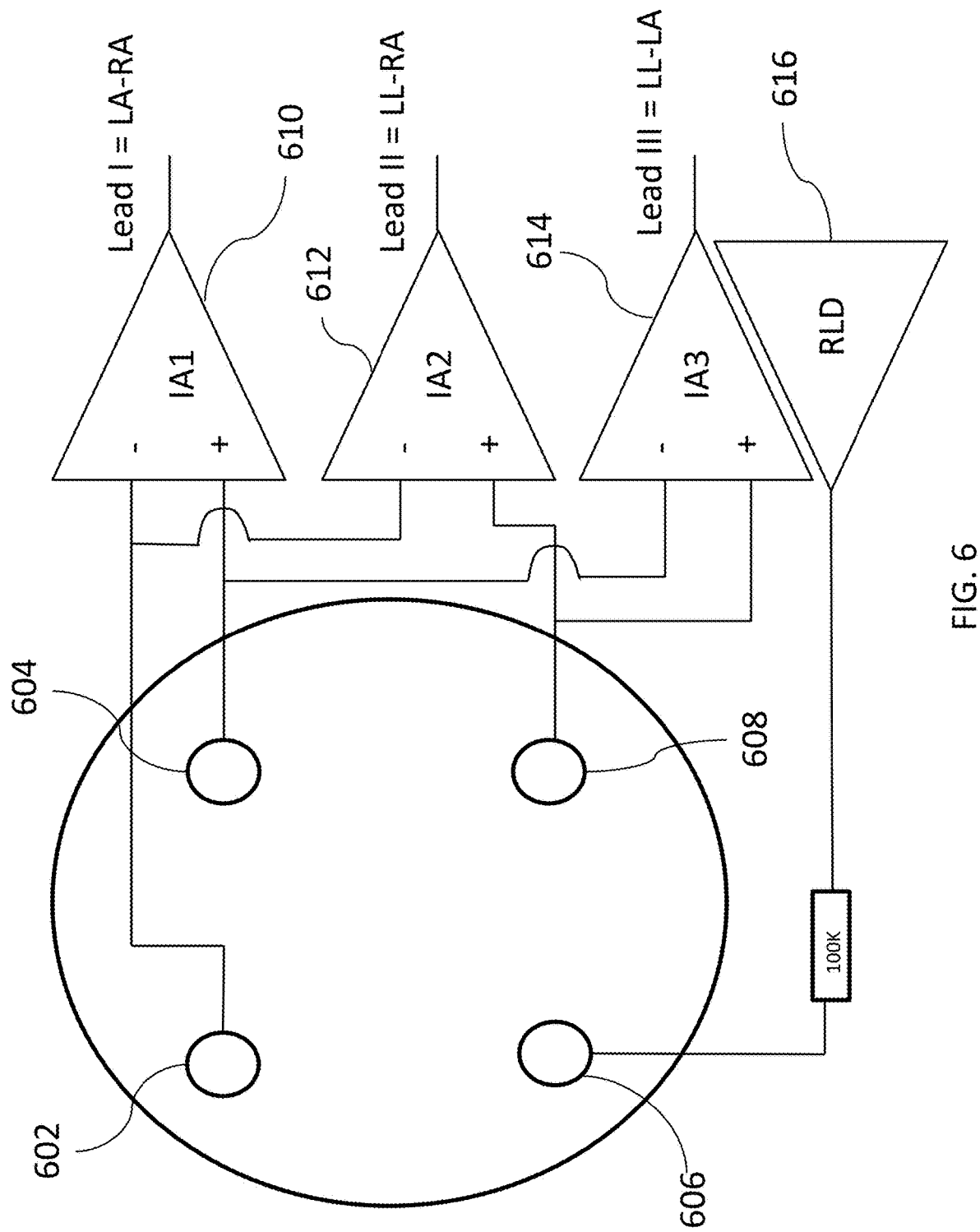
FIG. 6 illustrates generation of limb leads using three IAs.

In some instances, IAs may amplify a difference between two input signal voltages (e.g., amplify a differential input). The IAs may be integrated into the patch. Alternatively, the IAs may be integrated into the clinical monitors. FIG. 6 illustrates generation of limb leads using three IAs. Electrode 602, 604, 606, and 608 may correspond each to the RA, LA, RL, and LL electrodes as designated in a conventional ECG. A wireless patch may accomplish lead-off detection for RA, LA, and LL, as previously described herein. The patch may comprise instrumentation amplifiers (IA) to generate the lead signals (e.g., Lead I, Lead II, Lead III signals). The first IA 610 may generate Lead I by measuring and amplifying difference between a signal from the LA electrode and the RA electrode. The second IA 612 may generate Lead II by measuring and amplifying difference between a signal from the LL electrode and the RA electrode. The third IA 614 may generate Lead III by measuring and amplifying difference between a signal from the LL electrode and the LA electrode. Signal from the RL electrode may be sent to a right leg drive (RLD) 616 for use in noise reduction. Acquisition of signals in a differential manner may have benefits. For example, noise of signal may be reduced (e.g., power supply pickup is rejected). Additionally, fewer IAs may be necessary, leading to lower data rate on the wireless link. The patch may contain at least one less IAs than a number of lead signals to be generated. In some instances, the patch may contain at most two IAs in order to generate three lead signals (e.g., Lead I, Lead II, and Lead III signals). In some instances, the number of IAs required for generation (e.g., acquisition) of a certain number of lead signals may be equal to the number of lead signals, one less than the number of lead signals, or two less than the number of lead signals.

Figure 7:
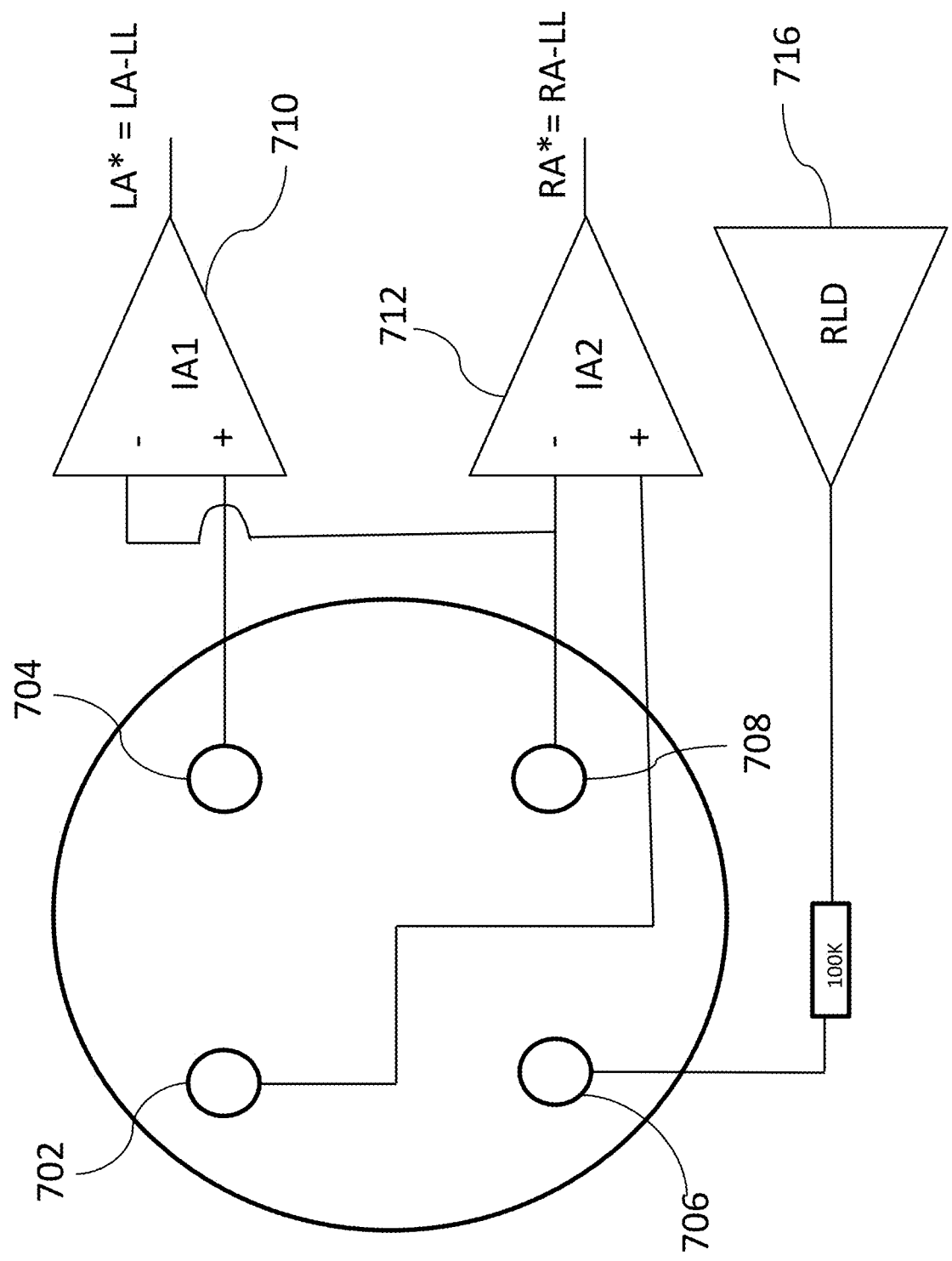
FIG. 7 illustrates acquisition of three lead signals with two IAs, in accordance with embodiments.

FIG. 7 illustrates acquisition of three lead signals with two IAs, in accordance with embodiments. Electrodes 702, 704, 706, and 708 may correspond each to the RA, LA, RL, and LL electrodes as designated in conventional ECG. A wireless patch may accomplish lead-off detection for RA, LA, and LL, as previously described herein. In some instances, RL lead off detection may result in lead off indication for RA, LA, and LL. The patch may comprise instrumentation amplifiers (IA) to generate the lead signals (e.g., Lead I, Lead II, Lead III signals). The first IA 710 may measure and amplify a difference between a signal from the LA electrode and the LL electrode, referred to as LA*. The second IA 712 may measure and amplify a difference between a signal from the RA electrode and the LL electrode, referred to as RA*. A signal from the RL electrode may be sent to a right leg drive (RLD) 716 for use in noise reduction. The signals generated and/or amplified by IAs may be transmitted (e.g., via a wireless link) and received at an adaptor.

Figure 8:
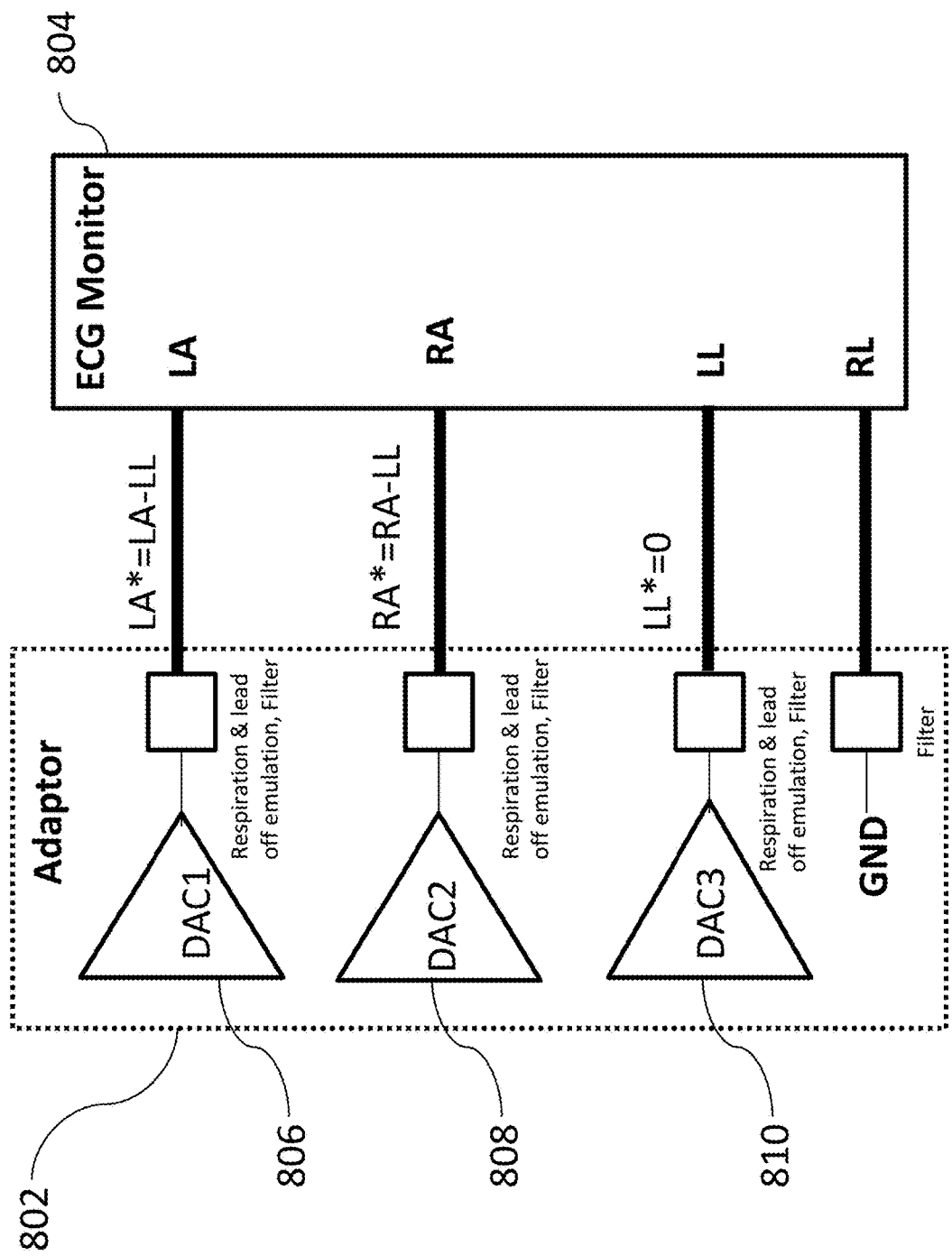
FIG. 8 illustrates an adaptor receiving signals and subsequent output to ECG monitor, in accordance with embodiments.

FIG. 8 illustrates an adaptor 802 for receiving and outputting signals to ECG monitor 804, in accordance with embodiments. The adaptor may comprise digital to analog converters (DACs). The DACs may convert data received over the wireless link in binary form (e.g., digital data) into an analog form for output to an ECG monitor. The adaptor may comprise a first DACs 806 outputting LA*, a second DAC 808 outputting RA*, and a third DAC 810 outputting LL*. LA* and RA* may refer to LA* and RA* as used with respect to FIG. 7. LL* may equal 0. For example, DAC 810 may have a constant input in a way such that the output of the DAC is always at zero voltage. LL* equaling 0 may mean that there is no signal level or that the signal level is always zero volts at all times. The ECG monitor may process the data in order to calculate limb leads and augmented limb leads. Using notations used in FIG. 7 limb leads and augmented limb leads may be calculated according to the following equations:

Lead $I = LA^* - RA^* = (LA-LL)-(RA-LL) = LA-RA$

Lead $II = LL^* - RA^* = 0 - (RA-LL) = LL-RA$

Lead $III = LL^* - LA^* = 0 - (LA-LL) = LL-LA$ $aVR = RA^* - \frac{1}{2}(LA^* + LL^*) = RA-LL-\frac{1}{2}(LA-LL-0) = RA - \frac{1}{2}(LA+LL)$ $aVL = LA^* - \frac{1}{2}(RA^* + LL^*) = LA-LL-\frac{1}{2}(RA-LL+0) = LA - \frac{1}{2}(RA+LL)$ $aVF = LL^* - \frac{1}{2}(RA^* + LA^*) = 0 - \frac{1}{2}(RA-LL+LA-LL) = LL - \frac{1}{2}(RA+LA)$ Additionally, respiration and pace maker signals may be calculated. For example, a user (e.g., a patient) may have a pace maker and a pace maker signal may be present along with ECG signals. The pace maker signal may be extracted at the patch end and be transmitted (e.g., wirelessly) to the adaptor. The pace maker signal may be added to ECG signals applied to monitor inputs. For example, the DACs may output a pace maker signal. In some instances, the third DAC (outputting LL*=0) may output the pace maker signal. In such a case, Lead I may be free of the pace maker signal but Lead II, Lead III, aVR, aVL, and aVF may comprise the pace maker signal (e.g., contain LL* as can be seen in the equations above). In some instances, the first DAC (outputting LA*) may output a pacemaker signal and the second DAC (outputting RA*) may output an inverted pacemaker signal. In such a case, all three limb leads and augmented limb leads may comprise the pace maker signal. In some instances, respiration may be calculated by injecting a current through ECG electrodes into a user's body and measuring resistance variations (e.g., in response to respiration). While measurement of respiration and pace maker has been described in the context of wireless patches comprising two IAs, any of the patches including wired patches and patches comprising zero, one, two, three or more IAs may measure the pacemaker signal and respiration.

Figure 9:
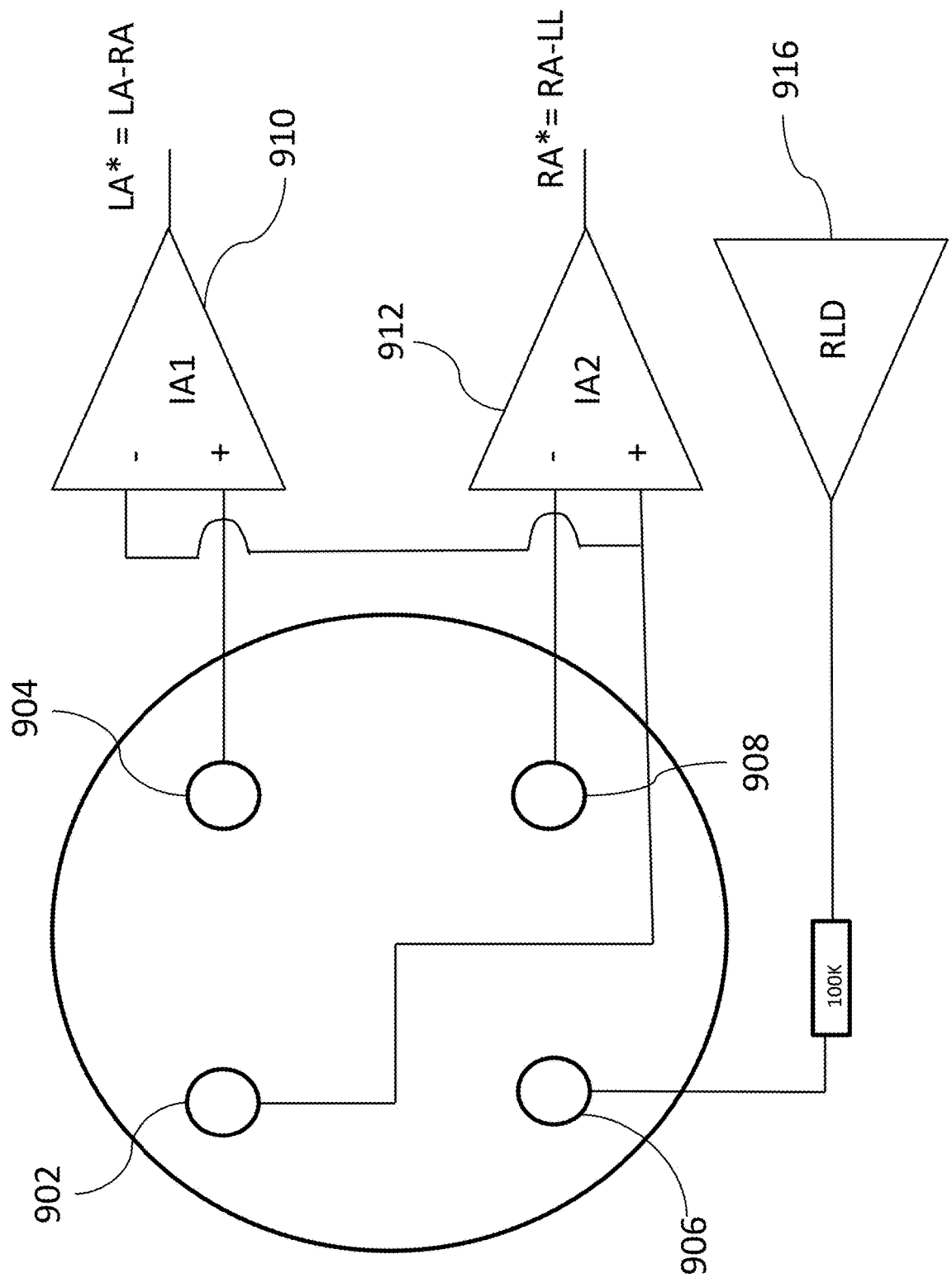
FIG. 9 illustrates an alternative set up for acquisition of three lead signals with two IAs, in accordance with embodiments.

FIG. 9 illustrates an alternative set up for acquisition of three lead signals with two IAs, in accordance with embodiments. Electrodes 902, 904, 906, and 908 may correspond each to the RA, LA, RL, and LL electrodes as designated in conventional ECG. A wireless patch may accomplish lead-off detection for RA, LA, and LL, as previously described herein. In some instances, RL lead off detection may result in lead off indication for RA, LA, and LL. The patch may comprise instrumentation amplifiers (IA) to generate the lead signals (e.g., Lead I, Lead II, Lead III signals). The first IA 910 may measure and amplify a difference between a signal from the LA electrode and the RA electrode, referred to as LA*. The second IA 912 may measure and amplify a difference between a signal from the RA electrode and the LL electrode, referred to as RA*. A signal from the RL electrode may be sent to a right leg drive (RLD) 916 for use in noise reduction. The signals generated and/or amplified by IAs may be transmitted (e.g., via a wireless link) and received at an adaptor. The adaptor may receive and output signals to an ECG monitor, substantially as described with respect to FIG. 8.

Acquisition of three lead signals via a patch comprising two IAs may be especially useful for wireless transmission of data. Because a small number of IAs are needed, data rate of a wireless link may be low and power consumption may be reduced. Additionally, because a small number of IAs are utilized, more space may be available for additional components within the patch. As signals are acquired in a differential manner (e.g., not single ended), power supply pick up may be rejected. In addition, the configuration may work well for acquisition of respiration and pace maker signals, for reasons described above.

Figure 10:
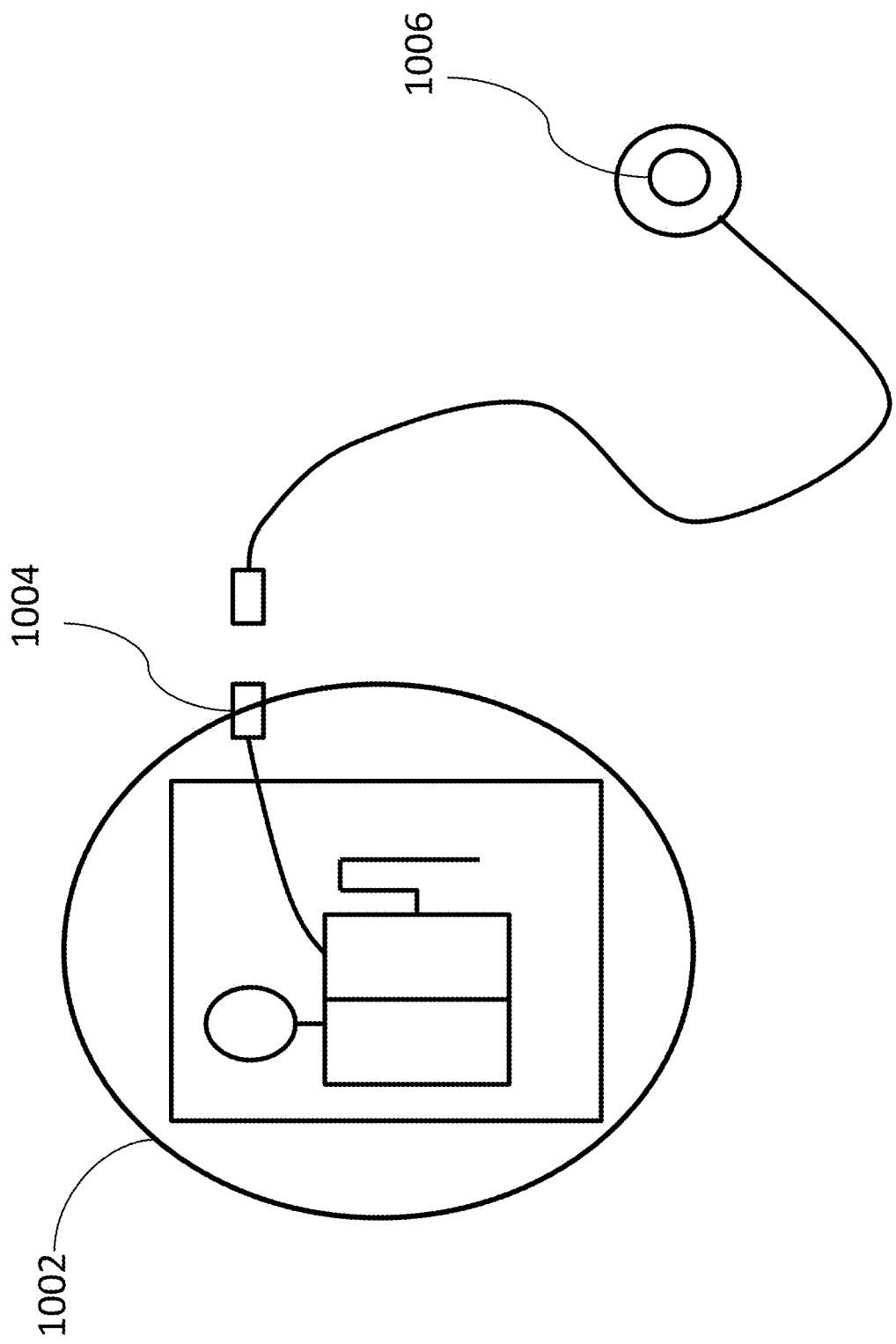
FIG. 10 illustrates a patch having a port for connection to an electrode, in accordance with embodiments.

In some instances the patch may communicate with one or more other patches or electrodes. FIG. 10 illustrates a patch 1002 having a port 1004 for connection to an electrode 1006, in accordance with embodiments. The electrode may be attachable (e.g. physically attachable) to the patch. The patch may be separable with the electrode. In some instances, the electrode may be removably attachable to the patch. While FIG. 10 shows one additional electrode to be connected to the patch, it is to be understood that one, two, three, four, five, six, or more electrodes may be configured to communicate with the patch. The port 1004 may be configured to be able to connect to any conventionally available electrode. The electrode may be utilized in acquiring other physiological data that may complement data acquired by the patch. For example, the electrode may be utilized in generating precordial leads, or V signals (e.g., as used in conventional ECG). Patch 1002 may be placed on a user as previously described herein (e.g., near a center of the chest in a specific orientation). Electrode 1006 in communication with the patch (e.g., via wires) may be placed on a user as a conventional V-electrode may be placed. Data acquired through the patch and/or the electrode in communication with the patch may be transmitted via wireless link to an adaptor (e.g., ECG monitor).

Figure 11:
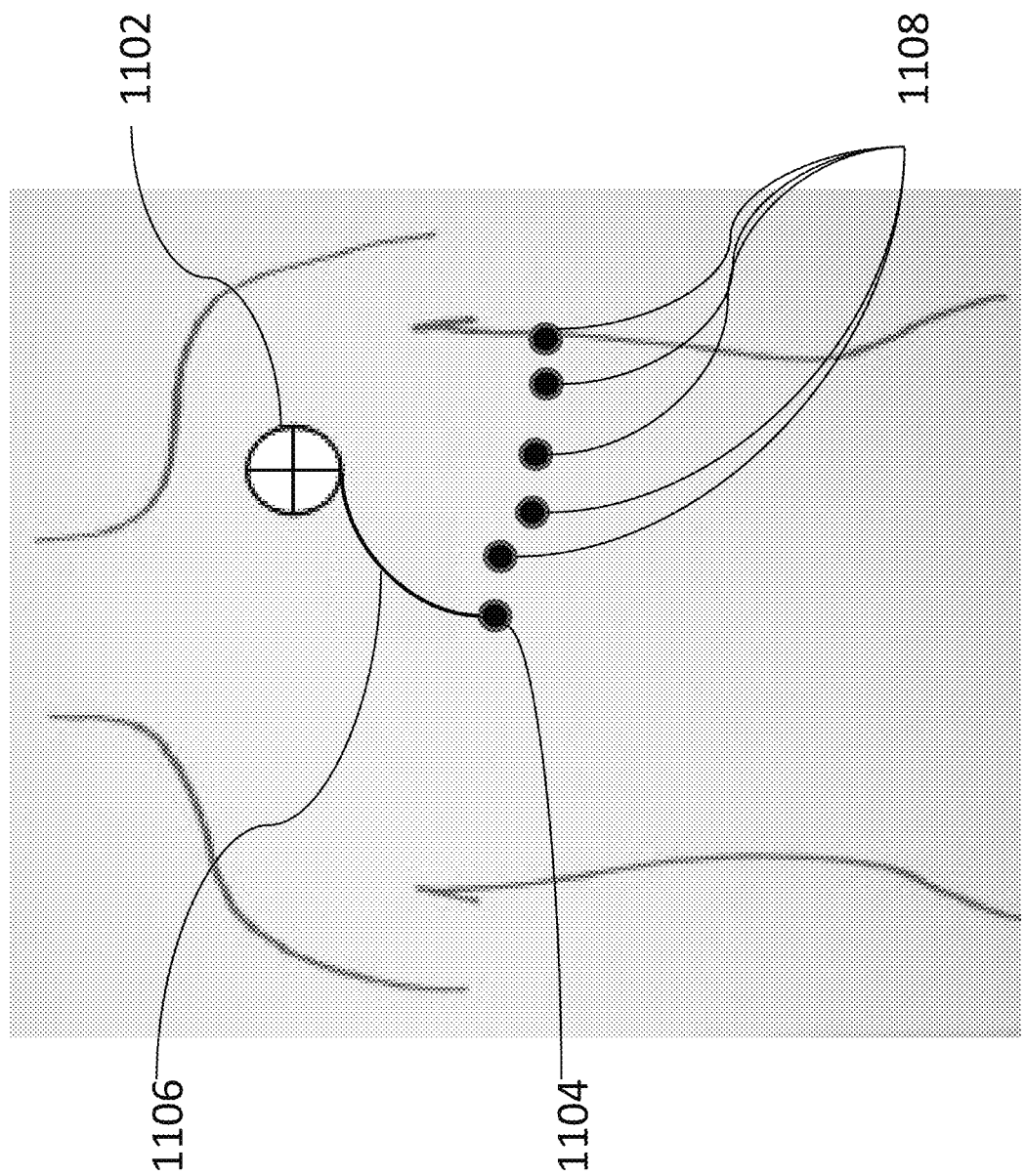
FIG. 11 illustrates a patch connected to an electrode with a wire acquiring data regarding limb leads, augmented limb leads, and precordial limb leads, in accordance with embodiments.

FIG. 11 illustrates a patch 1102 connected to an electrode 1104 using a wire 1106 acquiring data regarding limb leads, augmented limb leads, and precordial limb leads. Data acquired at the electrode may be transmitted to the patch using the wire. The electronic module of the patch may gather data acquired by the patch and/or data acquired by external devices (e.g., the electrode) in communication with the patch. The gathered data may be sent to an external device (e.g., adaptor, clinical monitor, etc) using a wireless link as previously described herein. Electrodes 1108 illustrate alternative positions the electrodes may be placed in order to gather information regarding precordial leads. While the patch 1102 is shown connected to one electrode 1104, the patch in some instances, may be connected to any combination of the electrodes 1104 and 1108 shown.

The patch may communicate with one or more external devices. The patch may communicate with the one or more devices through wired connections or wireless connections (e.g., radio, wifi, Bluetooth, etc). In some instances, two wireless devices may be used, one at the patch and one at the external device. The two wireless devices may form a wireless link that can be used for communication. For example, the patch may communicate with a clinical monitor (e.g., ECG monitor) as previously described herein. In some instances, the patch may have both wired and wireless capabilities. For example, the patch may communicate with an electrode (e.g., for generation of precordial leads) through a physical connection (e.g., via wires) and data acquired using the patch and the electrode may be transmitted using wireless communication. In some instances, the patch may communicate with a plurality of external devices. For example, a wireless device on the patch may be configured to communicate with a plurality of external devices such as computers, clinical monitors, gadgets, mobile devices (e.g., cell phones), PDAs, tablets, fitness trackers, etc.

In some instances, the patch may be configured to automatically upload data from the patch to an external storage medium (e.g., to a computer, cloud storage, memory, etc). In some instances, uploaded data may be automatically analyzed using one or more processors (e.g., using computer algorithms). Depending on the analysis, an alert may be sent to the user. For example a visual, auditory, or haptic warning may be sent to a user (e.g., on the patch). For example, a visual, auditory, or haptic warning may be sent to an external device in communication with the one or more processors (e.g., cell phone, computer, etc). In some instances, depending on the analysis, data may be sent to a healthcare professional for further analysis. In some instances, the patch may be configured to automatically send data from the patch to a healthcare professional or a clinical monitor.

Figure 12:
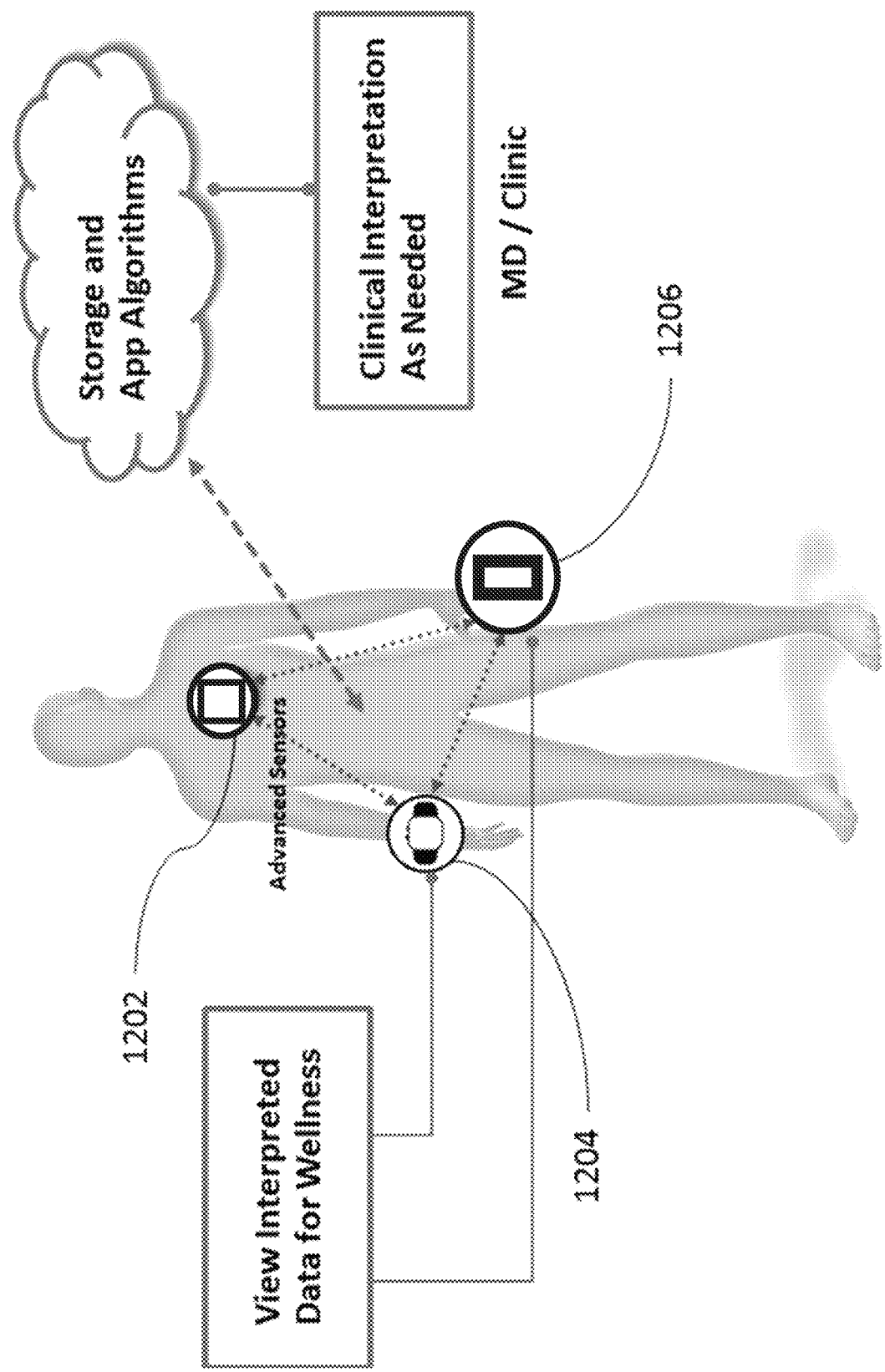
FIG. 12 illustrates an open patch platform communicating with other devices, in accordance with embodiments.

FIG. 12 illustrates an open patch platform 1202 communicating with other devices, in accordance with embodiments. The open patch platform may comprise a patch described throughout the application. The patch may comprise advanced sensors able to gather more data than conventionally available basic sensor 1204. The patch may monitor various physiological parameters. For example, the patch may be configured for 6-wave ECG monitoring. The patch may be configured to collect data regarding three limb leads and three augmented limb leads. The patch may be configured to connect to (e.g., physically be coupled to) additional electrodes such that precordial leads may be generated as well. The patch may monitor heart rate and respiration of a user, as previously described herein. In some instances, the patch may monitor acceleration, hydration, temperature, SpO2, blood pressure. The patch may be configured for ambulatory monitoring. The patch may monitor a motion, location, audio, video, pressure of the/around the user.

In some instances, gathered data (e.g., using the open patch platform) may be interpreted using an on-board processor (e.g., on the electronic module) or an off-board processor such as a processor on external device 1206. The interpreted data may be displayed on a display. For example, the interpreted data may be displayed for view on a display of the basic sensor and/or external device. The interpreted data may be used to send an alert (e.g., to the user or a healthcare professional) or may be sent elsewhere for further processing and/or analysis. In some instances, interpreted data displayed may be data regarding a user's wellness. In some instances, gathered data may be stored (e.g., on a memory, cloud storage, etc). The stored data may be sent to a healthcare professional or be accessed by a healthcare professional for clinical interpretation as needed.

In some instances, different patches may be configured to monitory different physiological parameters. The different patches may be swapped in and out depending on desired a physiological parameter to monitor. In some instances, a patch may comprise modular components. For example, the patch may comprise a port to which other external devices or components may be connected to. The external devices and/or components may provide additional functionality to the patch. For example, a patch may be configured for 6-wave ECG monitoring while additional devices that are connected to the patch may be configured to monitor acceleration, temperature, and hydration of a user. The additional devices may connect to the patch via wired or wireless communication. In some instances, a single patch may be configured to monitor the various physiological parameters.

The patch may be configured to work together with applications (e.g., computer algorithms). For example, the patch may be capable of monitoring various physiological parameters and specific applications may be played (e.g., selected by a user to be executed) in order to gather a subset of the physiological parameters. A single application may be executed and a physiological parameter may be selected within the application that a user desires to monitor. In some instances, different applications may be executed to monitor different physiological parameters. Selecting a subset of the various physiological parameters may save resources on the patch such as power and battery. In some instances, different applications may be configured to work with different patches (e.g., having different capabilities) and/or different external devices. The applications may be executed on the patch. Alternatively, the applications may be configured to be executed on external devices in communication with the patch (e.g., computer, fitness tracker, cell phone, etc).

Figure 13:
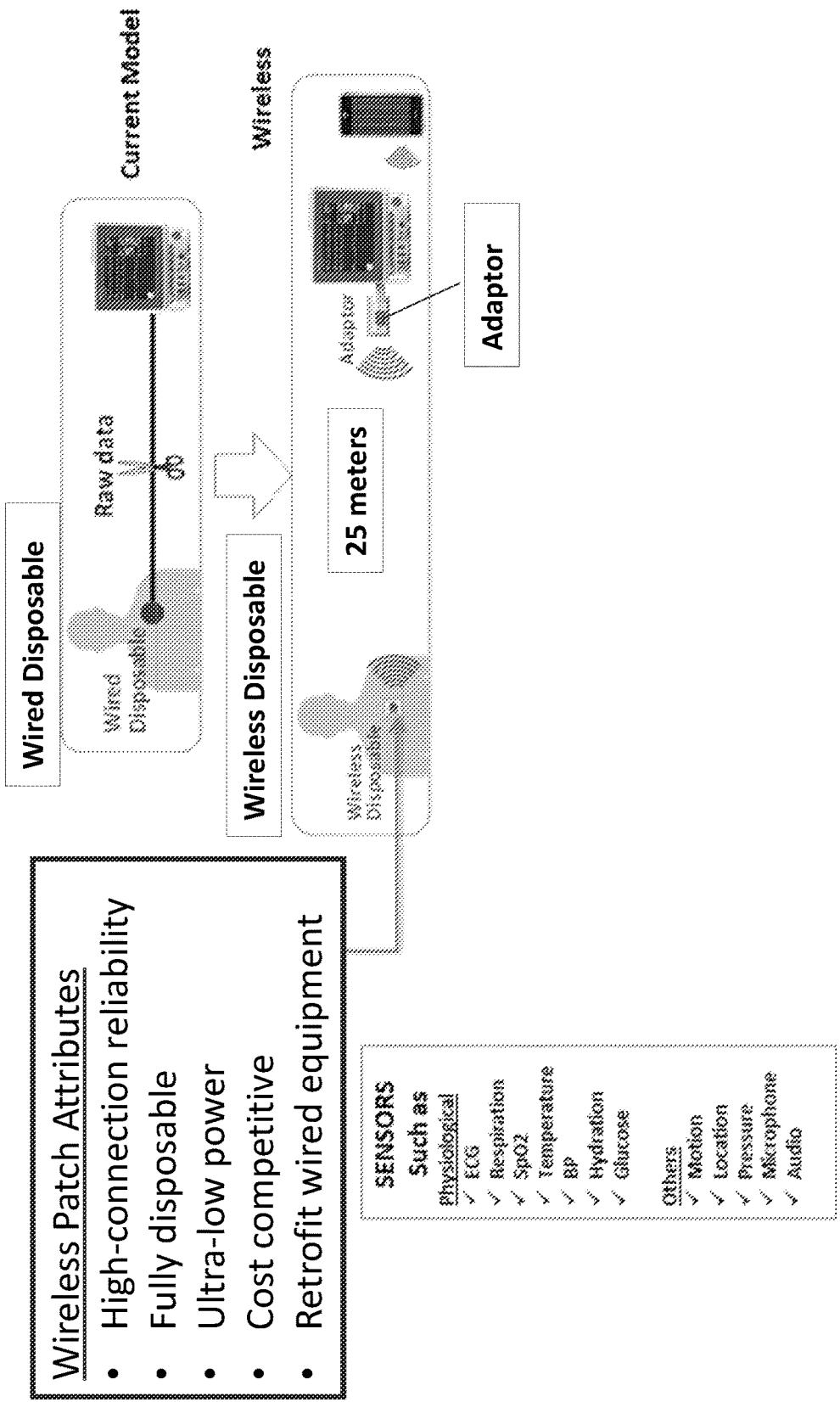
FIG. 13 illustrates wired and wireless patch systems, in accordance with embodiments.

FIG. 13 illustrates wired and wireless patch systems as previously described herein. A wireless patch may have high-connection and reliability. A wireless patch may be as reliable or more reliable than a wired patch. A wireless patch may be more reliable than a wired patch due to absence of the wires. A wireless patch may operate wirelessly for up to 10 m, 15 m, 20 m, 25 m, 30 m, 35 m, 40 m, 50 m, 55 m, 60, 70 m, 80 m, 90 m, 100 m, or more away from an adaptor as previously described herein. A wireless patch may be fully disposable. A wireless patch may be partially disposable. For example, only the electronic module (e.g., as previously described herein) may be preserved while other components are disposed. For example, only the electronic module may be disposed of while other components are preserved. In some instances, the electronic module of a wireless patch may be replaced with, or switched out for other electronic modules comprising alternative, and/or additional features. The other electronic modules may comprise alternative, and/or additional sensors. A wireless patch may be ultra-low powered. A wireless patch may be cost competitive. A wired monitoring system may be retrofit to enable wireless communication. A wired or wireless patch as described herein may monitor physiological parameters such as ECG, respiration, SpO2, Temperature, Blood Pressure, Hydration, and/or glucose. A wired or wireless patch as described herein may monitor motion, location, pressure, and/or audio (e.g., of a user or environment around the patch).

Figure 14:
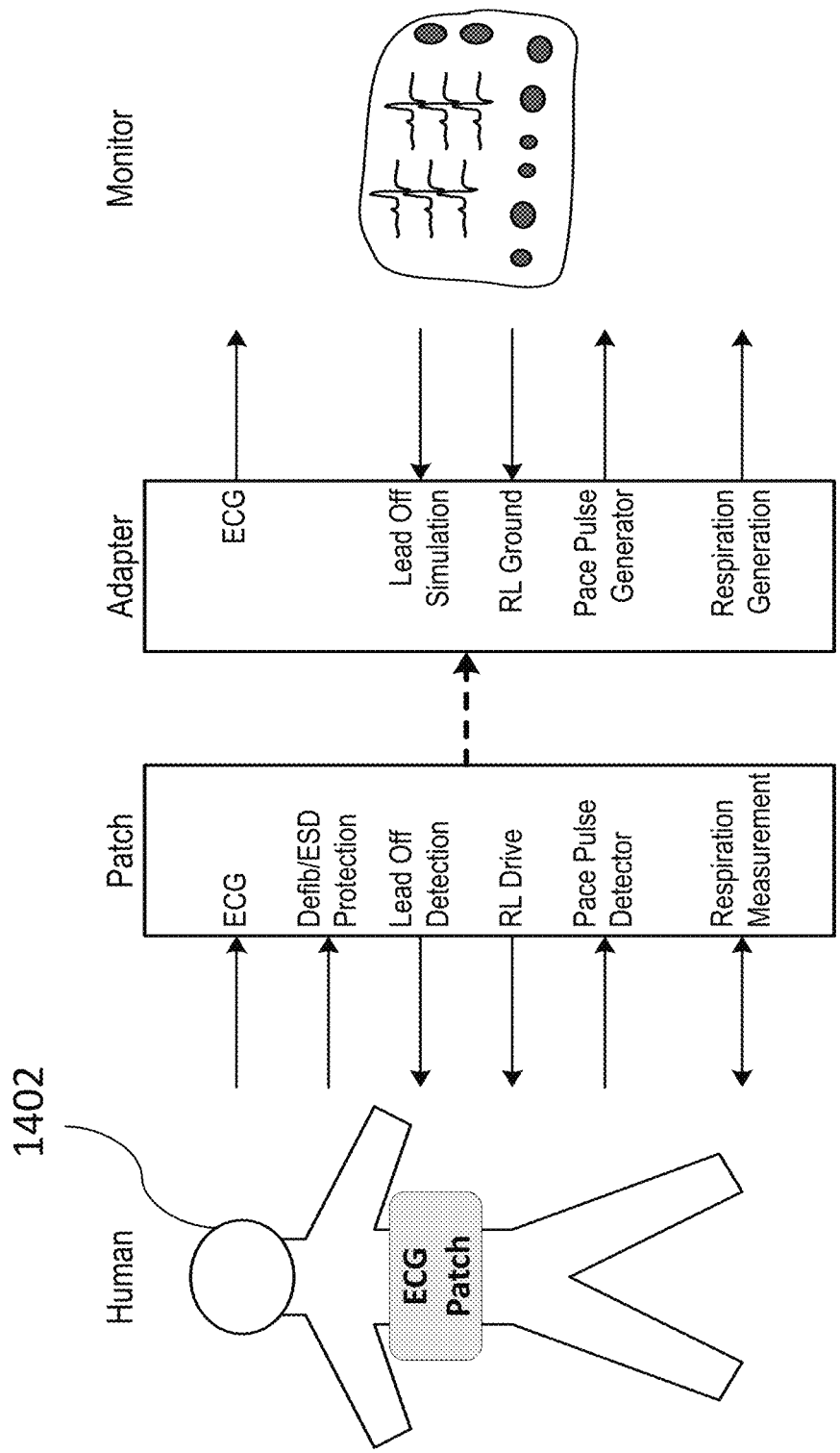
FIG. 14 illustrates wireless patch/receiver systems for patient monitoring, in accordance with embodiments.

FIG. 14 illustrates a wireless patch/receiver system for patient monitoring, in accordance with embodiments. The patch may be placed on a user 1402, such as a patient requiring monitoring. The patch may be used for lead off detection. The patch may provide lead-off detection to the patient. The patch may be used to acquire ECG data. The patch may provide defibrillation and/or ESD protection. The patch may be used to provide a RL drive. The patch may be used to detect a pace maker pulse. The patch may be used for respiration measurement, as previously described herein. The patch may be used to acquire any other data described elsewhere (e.g., SpO2) as necessary. Data acquired by the patch may be transmitted (e.g., wirelessly) to an adaptor as described elsewhere. The adaptor may generate data regarding ECG, pace maker pulse, respiration, etc. The generated data may be viewed by the patient or a healthcare professional.

Figure 15:
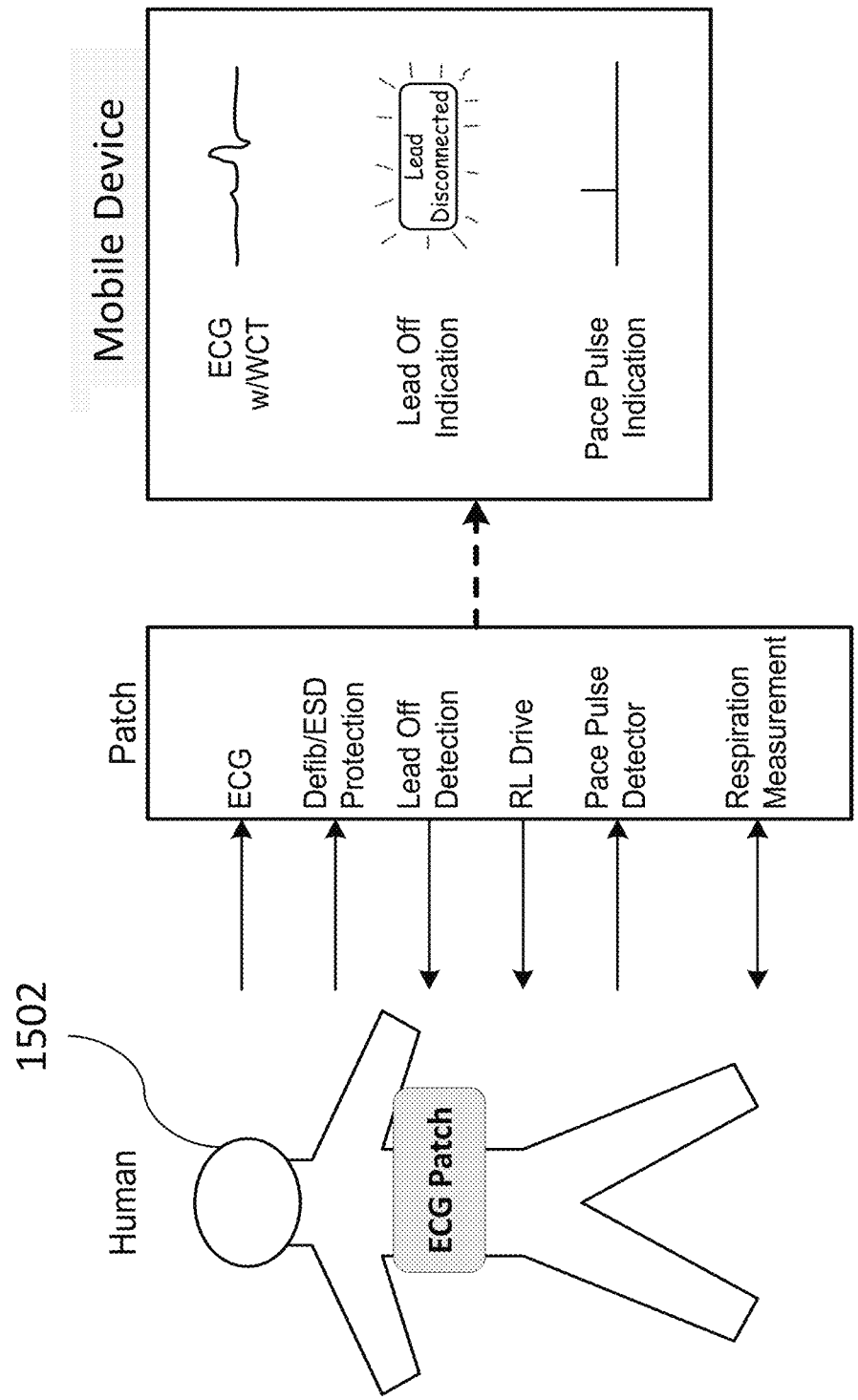
FIG. 15 illustrates wireless patch/mobile device systems, in accordance with embodiments.

FIG. 15 illustrates a wireless patch/mobile device system, in accordance with embodiments. The patch may be placed on a user 1502. The user may be an ordinary user participating in everyday activities, or a sports related activity. The patch may be used for lead off detection. The patch may provide lead-off detection to the patient. The patch may be used to acquire ECG data. The patch may provide defibrillation and/or ESD protection. The patch may be used to provide a RL drive. The patch may be used to detect a pace maker pulse. The patch may be used for respiration measurement. The patch may be used to acquire any other data described elsewhere (e.g., SpO2) as necessary. Data acquired by the patch may be transmitted (e.g., wirelessly) to a mobile device as described elsewhere. The mobile device may generate data or display data regarding ECG (e.g., ECG with WCT), lead-off detection, pace maker pulse signals, etc.

Figure 16:
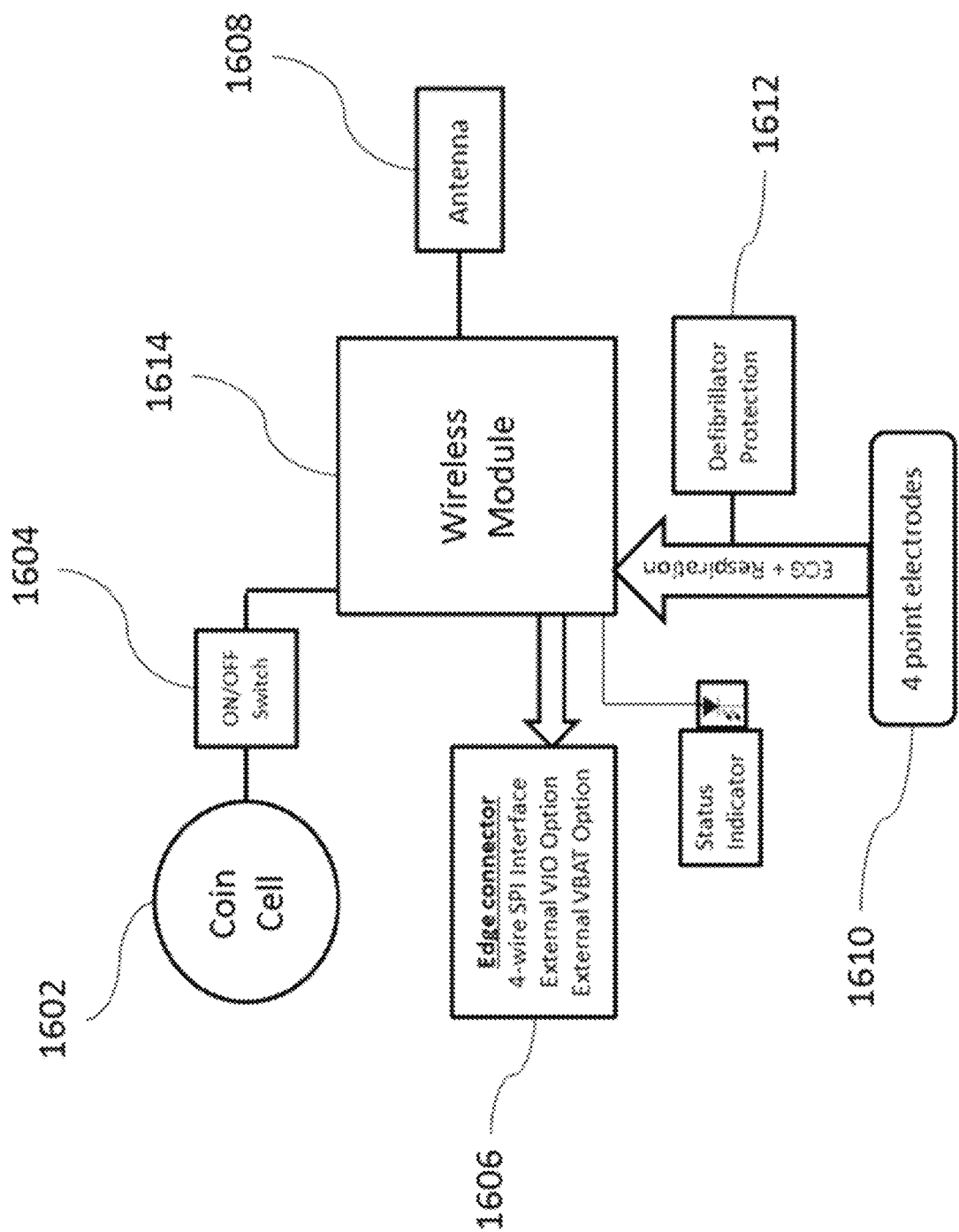
FIG. 16 illustrates electronics for a patch, in accordance with embodiments.

FIG. 16 illustrates electronics for the patch, in accordance with embodiments. The electronics may comprise a plurality of components, such as a coin cell 1602, on/off switch 1604, edge connector 1606, antenna 1608, electrodes (e.g., four point electrodes) 1610, defibrillator protectors 1612, and/or wireless modules 1614. The edge connector may comprise a four-wire SPI interface, an external VIO option, and/or an external VBAT option. The electronics for the patch may all be integrated within the patch. In some instances, at least a part of the electronics may be located on or within the electronic module. The electronic module may comprise a coin cell, on/off switch, edge connector, antenna, electrodes, defibrillator protectors, and/or wireless modules. In some instances, some components of the electronics may be located off-board the patch. In some instances, some components of the electronics for the patch may be switched out for other electronics with different functionalities, as previously described herein.

Figure 17:
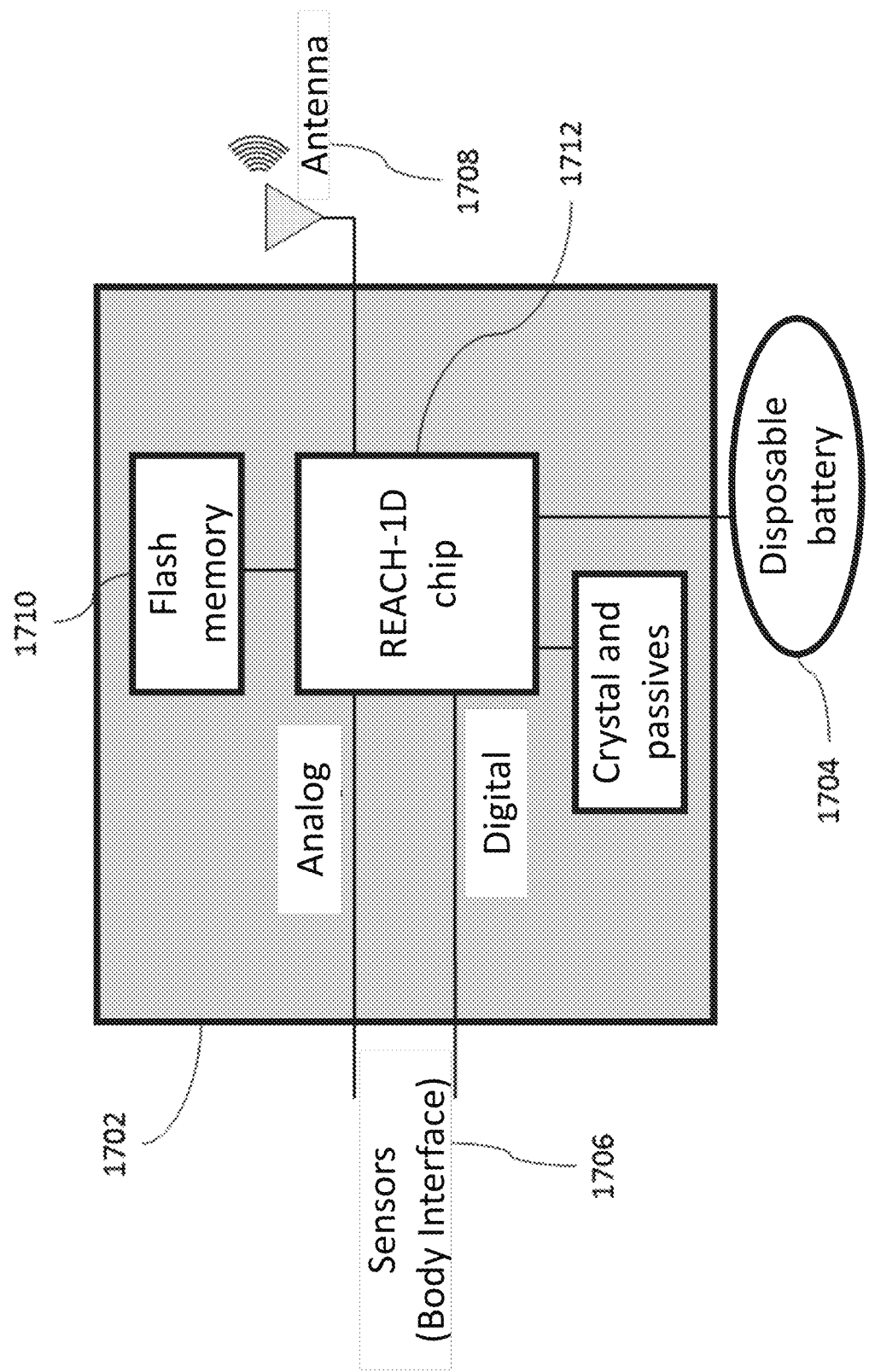
FIG. 17 illustrates a wireless module of a patch, in accordance with embodiments.

FIG. 17 illustrates a wireless module 1702, in accordance with embodiments. The wireless module may enable communication with an external device, such as the adaptor or mobile device previously described herein. The wireless module may comprise a plurality of components. The wireless module may be in direct communication with an electronic component of the patch, such as the batter 1704, sensors (e.g., body interfaces) 1706, and/or antennas 1708. The wireless module may comprise a flash memory 1710. The flash memory may store (e.g., temporarily or permanently) acquired data from the patch. The wireless module may comprise a chip, such as a REACH-1D chip 1712. A REACH-1D chip may intake analog signals and convert it to digital signals. A REACH-1D chip may intake digital signals and convert it to analog signals. The signals (e.g., digital or analog signals) may be transmitted to an external device or component (e.g., adaptor or mobile device) through a wired or wireless connection. In some instances, digital signals may be transmitted via a wireless connection.

FIG. 18 illustrates a patch design, in accordance with embodiments. In some instances, the patch may be a foldable patch. The patch may comprise a single substrate with folds. For example, various external housing components of the patch may be constructed of a single mold. For example, the cover, base, and/or spacer as previously described herein may be constructed on a single mold. For example, FIG. 18 shows a base 1802, cover 1804, and spacer 1806, 1808, 1810 made of a single mold. The patch may comprise a plurality of substrate components that may be folded onto (e.g., on top of) one another. For example, the patch may comprise substrate components 1802, 1804, 1812, and 1814 that may be folded on top of one another. The plurality of substrate components may be made of a single mold. Each of the substrate components may be configured to support (e.g., receive, house, comprise) different electronic components of the patch. In some instances, a substrate component may not be configured to support an electronic component, e.g., substrate component 1804. For example, substrate component 1812 may be configured to support electrodes, and/or ECG gel cups. For example, substrate component 1814 may be configured to support a coin battery and/or UWB antennas. For example, component 1802 may be configured to support a processor or ASIC module. Each of the electronic components may be in communication with one another, e.g., through conductive traces. The conductive traces may traverse through each substrate components. The conductive traces may traverse through each substrate components comprising or supporting an electronic component.

FIG. 19 illustrates two different perspectives of a blown up view of a patch design, in accordance with embodiments. View 1901 shows the exploded patch viewed from above while view 1903 shows the exploded patch from viewed from below. The patch may comprise a cover 1902, a base 1904, and a spacer 1906 configured to house electronic module 1908. The electronic module is shown coupled to electrodes 1910, 1912, 1914, and 1916 through intermediary structure 1918. The spacer may be further configured to be coupled to the cover and the base. The spacer may define a space in which the electronic module is to be located in and separates the base from the cover. The patch may further comprise cutouts 1920 and gels 1922 as previously described herein.

Figure 20:
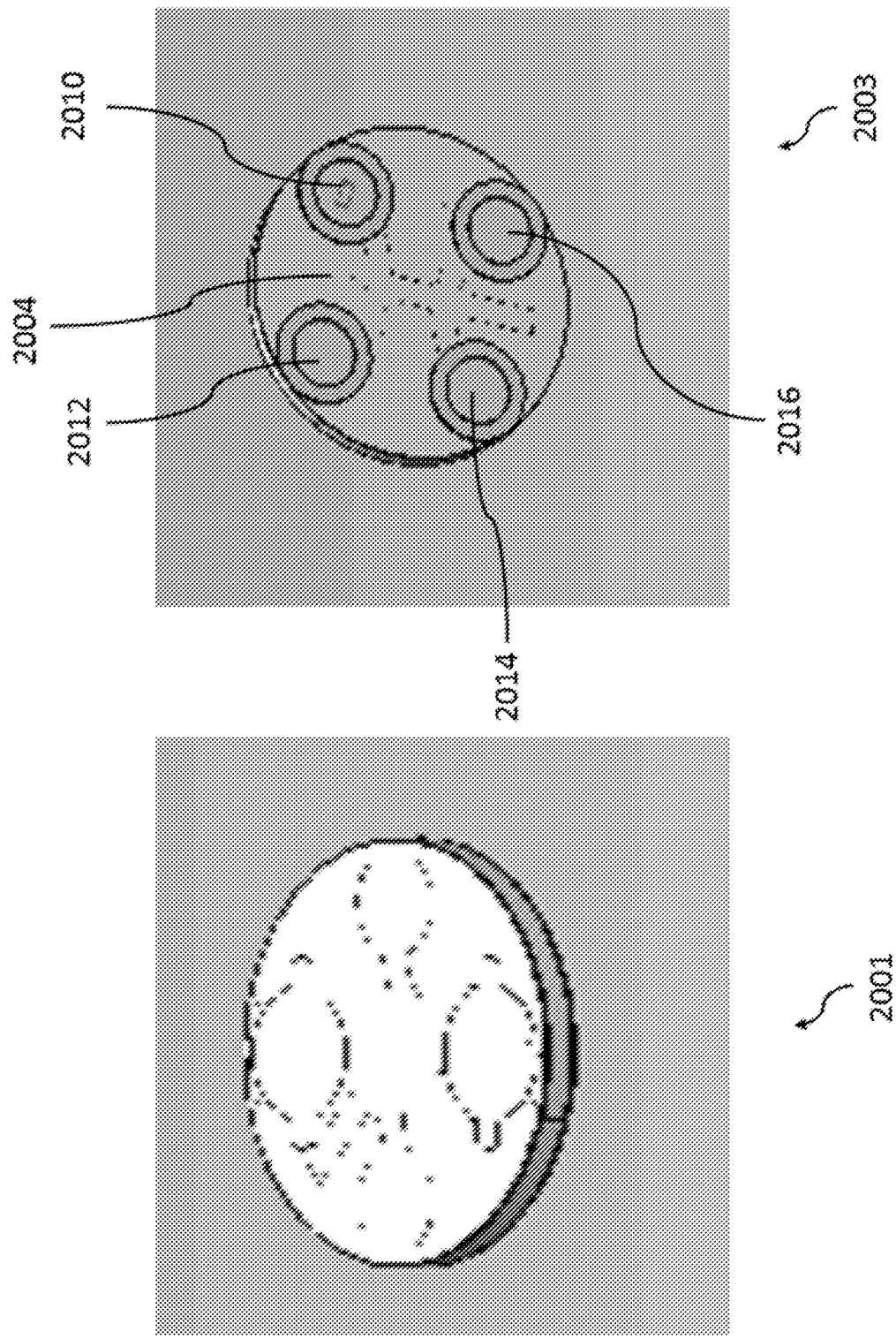
FIG. 20 illustrates a working configuration of the patch design of FIG. 19 from two different perspectives, in accordance with embodiments.

FIG. 20 illustrates a working configuration of the patch design of FIG. 19 from two different perspectives, in accordance with embodiments. View 2001 shows the patch from above while view 2003 shows the patch from below. Electrodes 2010, 2012, 2014, and 2016 can be seen on (e.g., through) base 2004. The base may comprise the electrodes.

Figure 21:
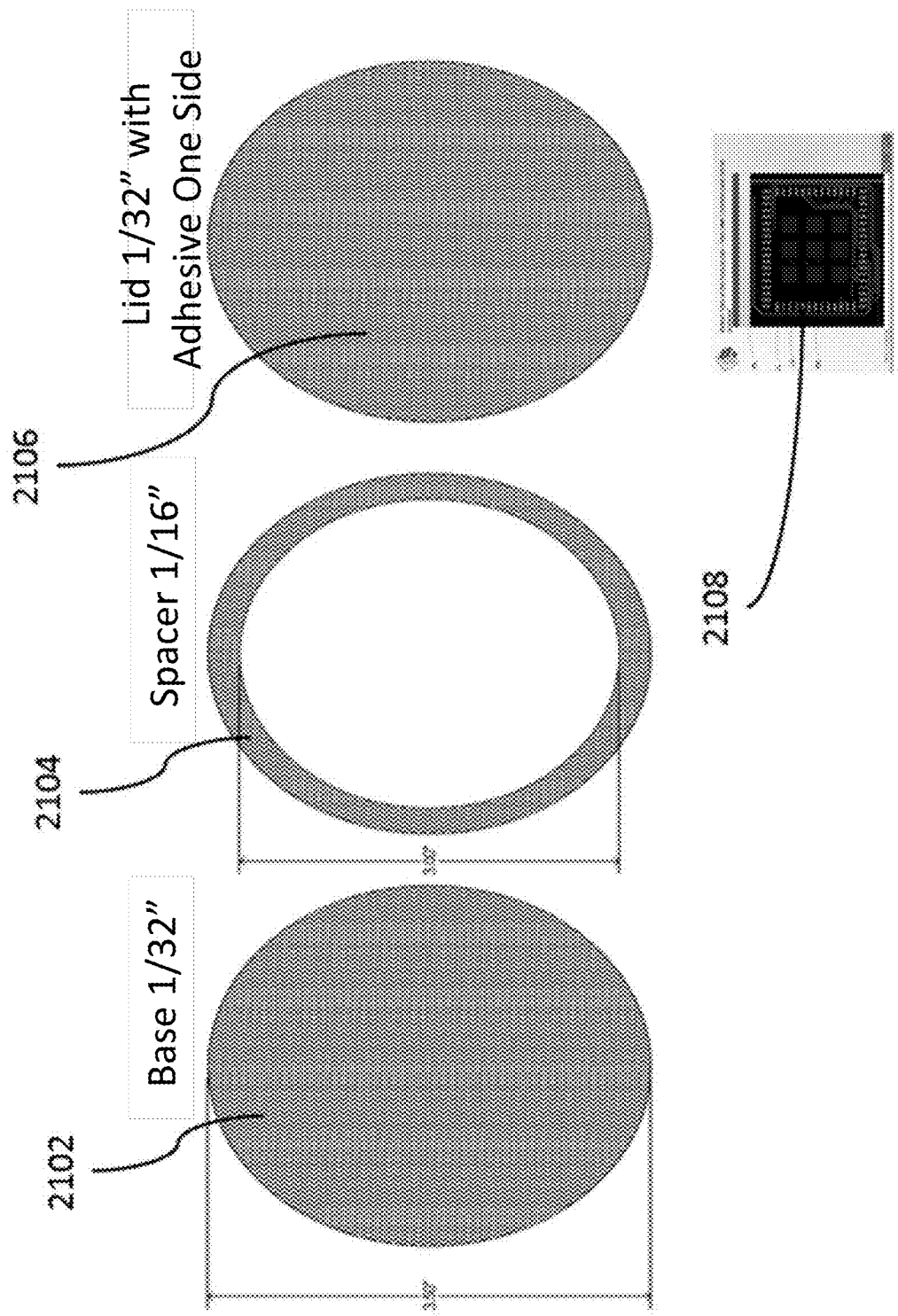
FIG. 21 illustrates a patch design, in accordance with embodiments.

FIG. 21 illustrates a patch design, in accordance with embodiments. In some instances, the base 2102, spacer 2104, and cover 2106 may be configured to be placed on top of the other. The electronic module 2108 may be disposed between the base and the cover, within a space defined by the spacer, substantially as described elsewhere.

Figure 22:
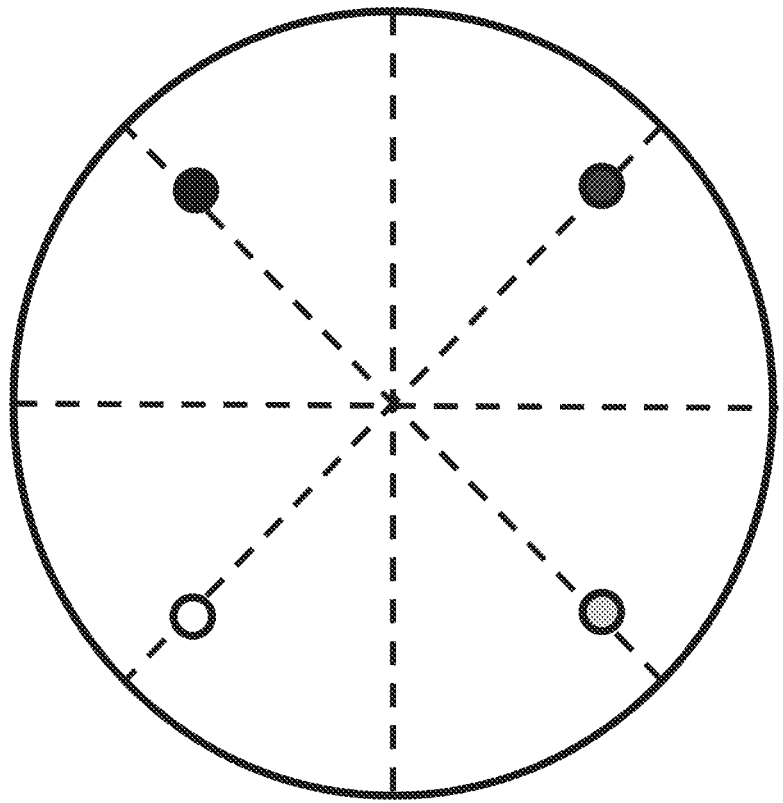
FIG. 22 illustrates a measurement template that may be used for marking areas where snaps will go.
Figure 23:
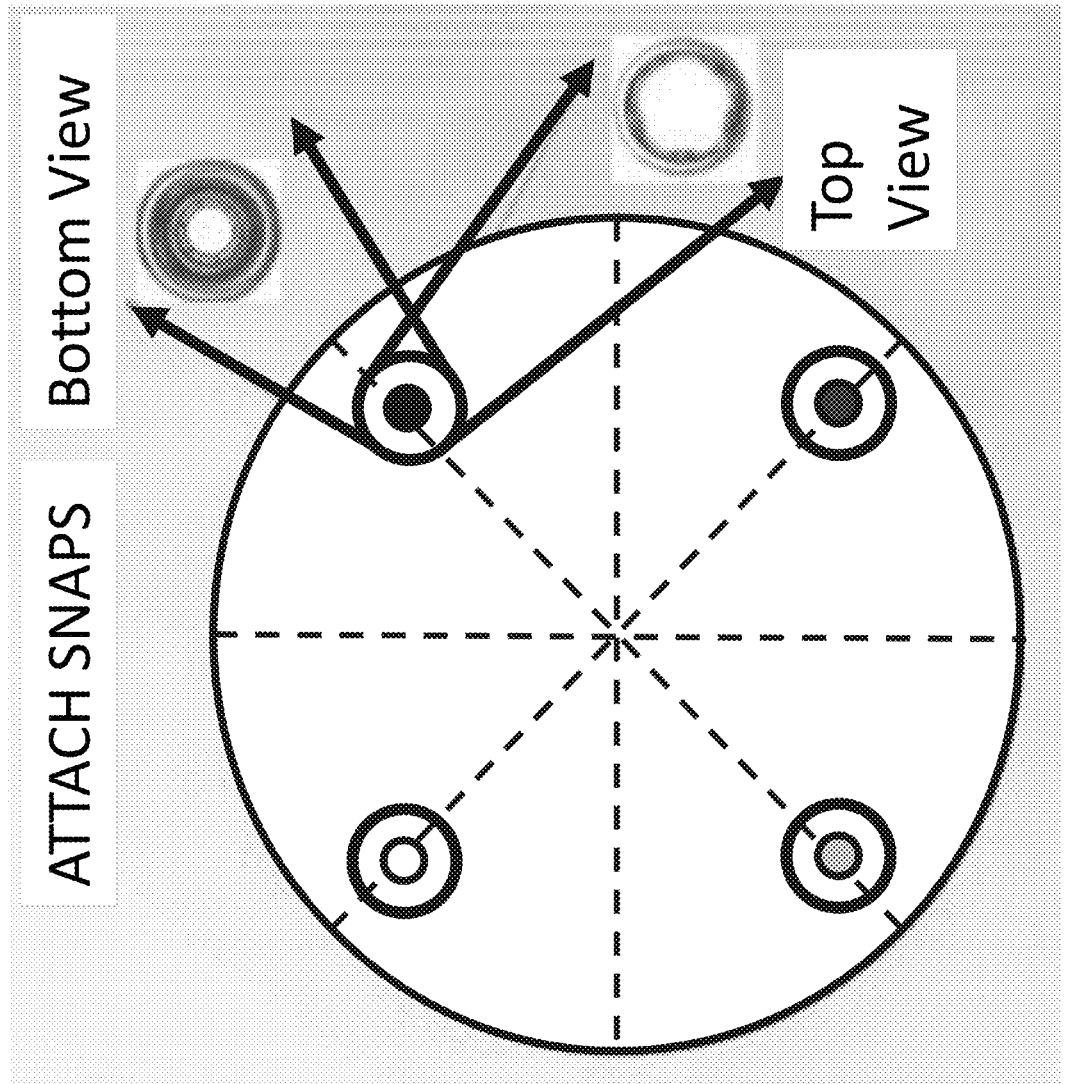
FIG. 23 illustrates a depiction that may be used for inserting a prong snap.
Figure 24:
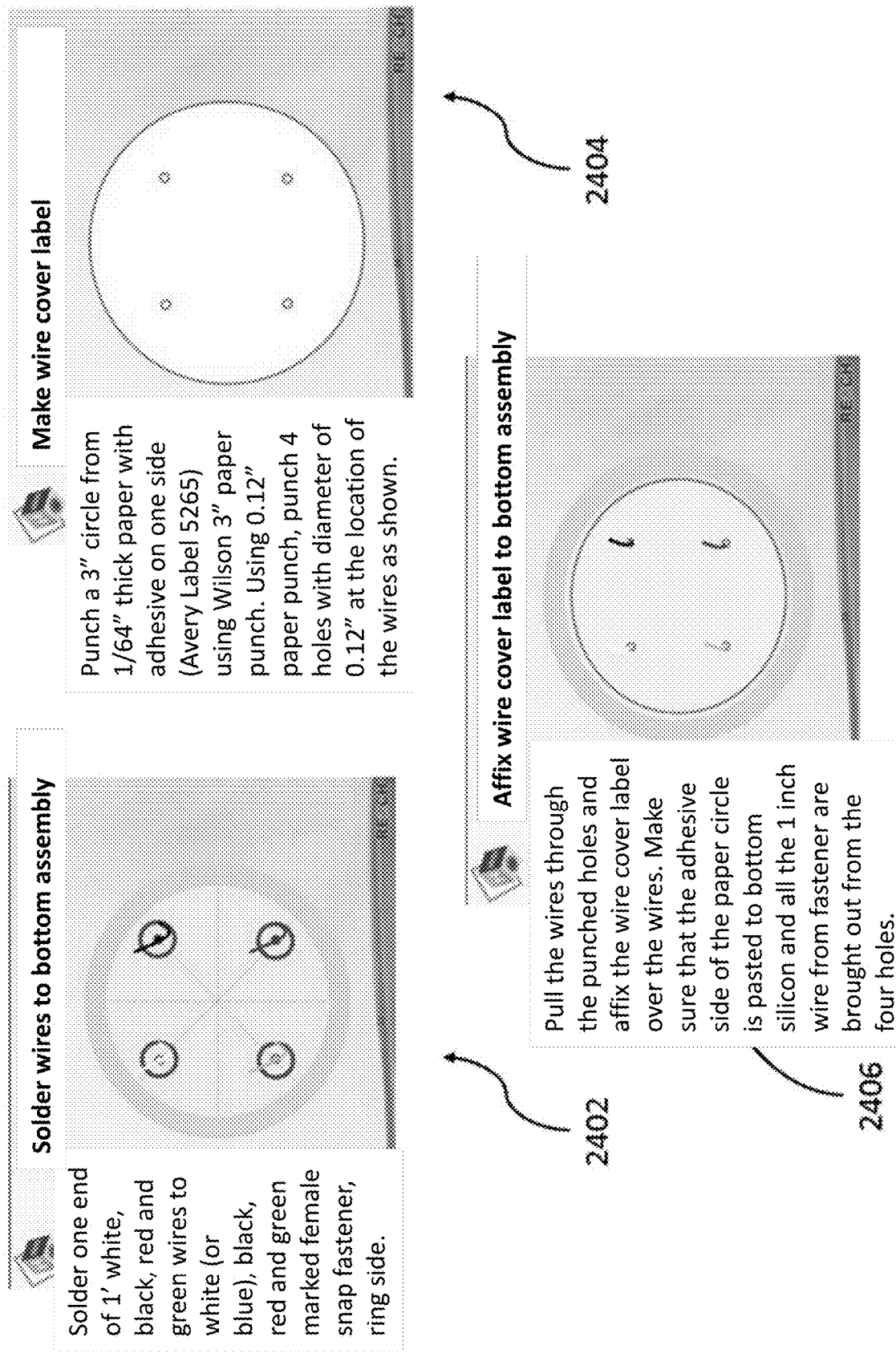
FIG. 24 depicts a first illustration showing wires soldered to a bottom assembly, a second illustration showing a wire cover label, and a third illustration showing the wire cover affixed to the bottom assembly.
Figure 25:
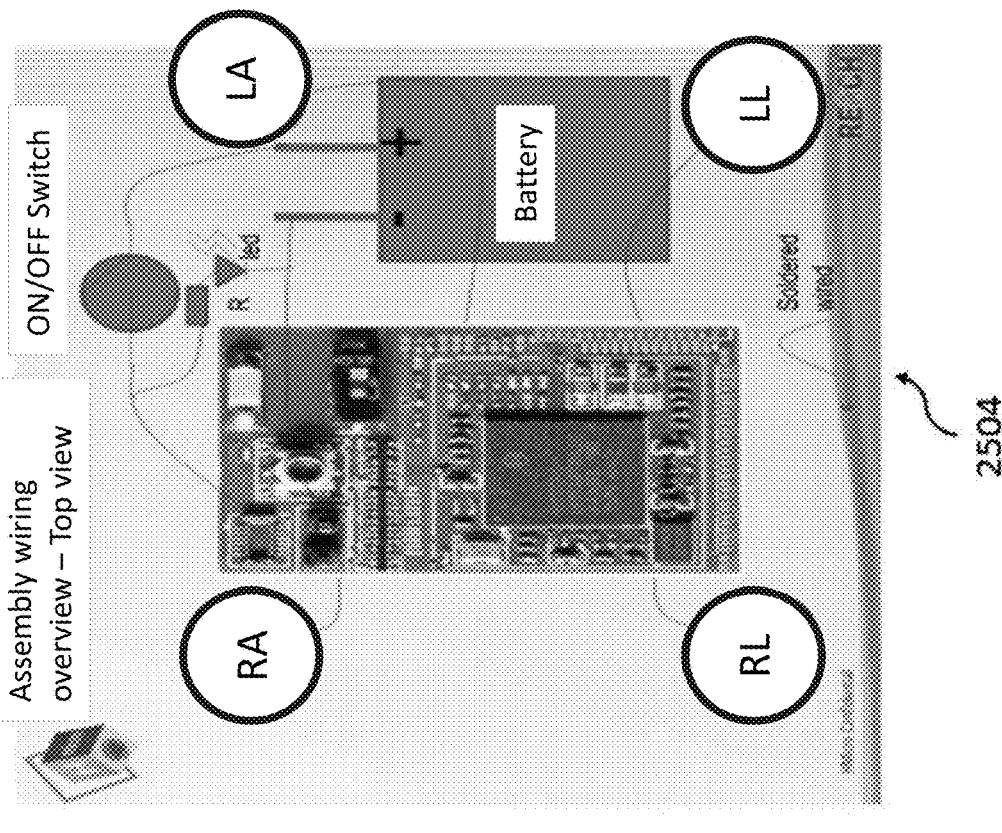
FIG. 25 illustrates a general view and detailed view of wire layout to the HMI module.
Figure 25:
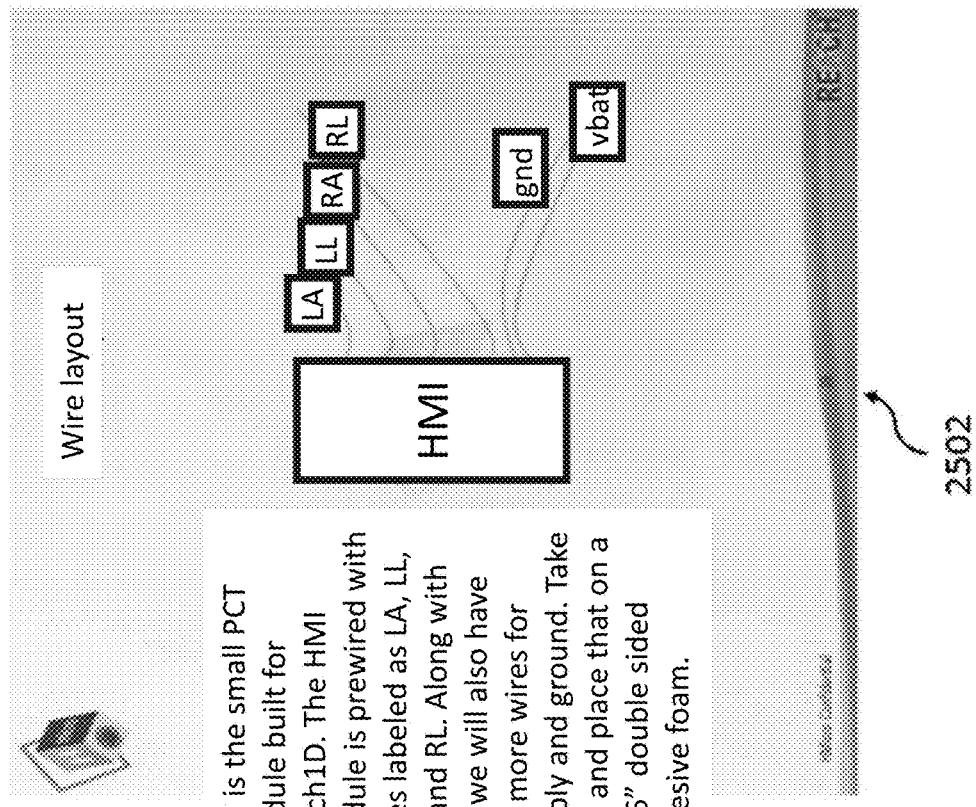
Figure 26:
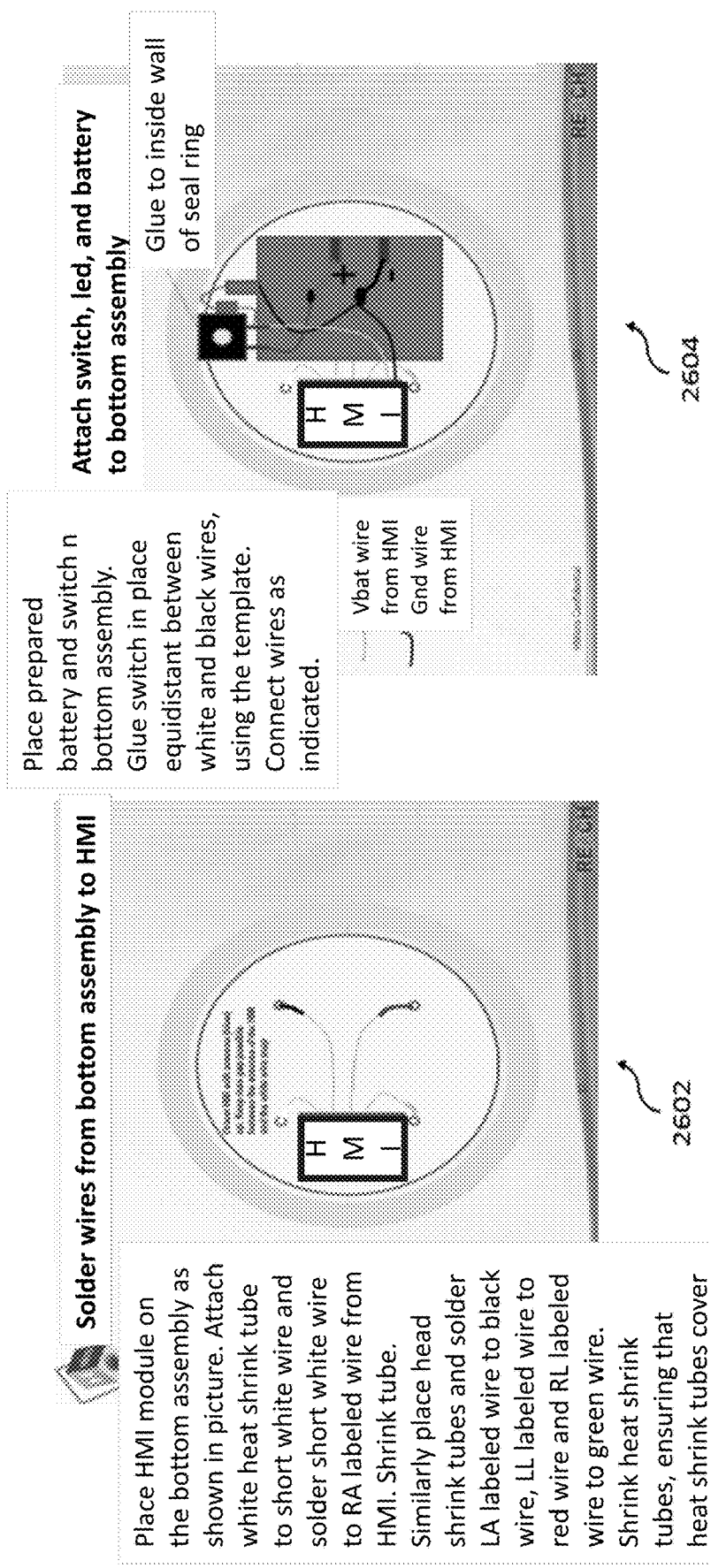
FIG. 26 illustrates HMI module attached to the bottom assembly in a first illustration and switch, led, and battery attached to the bottom assembly in addition to the HMI module in a second illustration.
Figure 27:
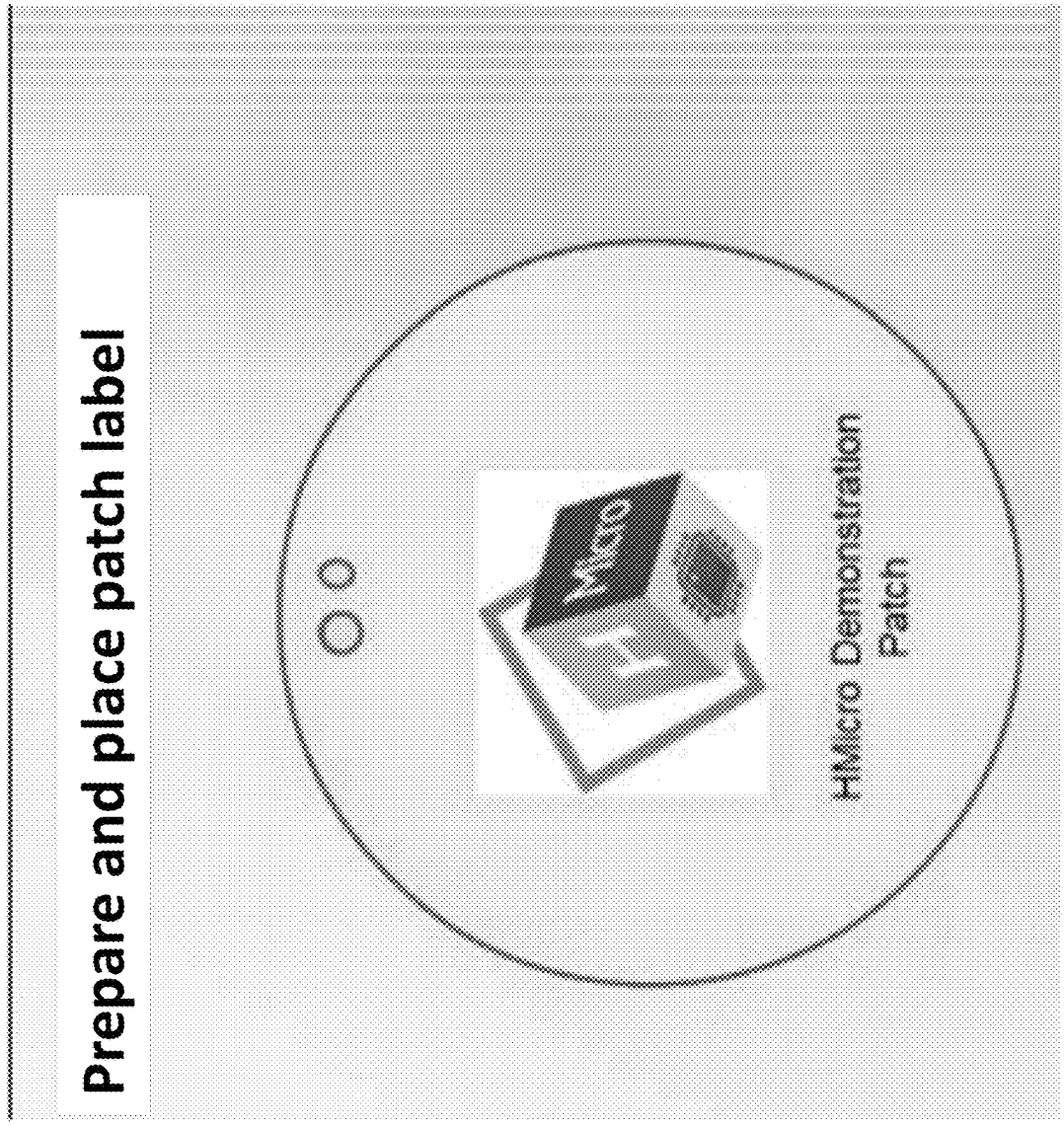
FIG. 27 illustrates a patch label that may be placed on the patch.

The patch may be constructed and tested according to the following exemplary, non-limiting instructions. 1) Obtain 4 inch by 36 inch strip of 1/32" silicone sheeting. 2) Place the sheeting on the poly cutting board. 3) Place the 3.5" punch over the area, allowing at least 1/2 inch on all sides. 4) Using the rubber mallet, hit the top of the punch and each side at least 2 times. 5) Twisting the punch to ensure that the silicone is cut through, carefully lift the punch and remove the 3.5" circle. 6) Inspect each circle to ensure that there aren't any tears on the outside or loose tags of silicone. 7) Clean silicone sheet with 70% IPA to ensure all powder is removed from silicone sheet. 8) Using a template and sharpies, mark the areas where the snaps will go. FIG. 22 illustrates a measurement template that may be used for marking areas where snaps will go. Use blue or white for white, black for black, red for red and green for green. Use a single small dot, just large enough to see. 9) Gather prong tools: blue prong tool, hammer, and pencil with eraser. 10) Using pencil and a prong snap component, and a depiction (e.g., FIG. 23) insert the prong snap from the underside of the circle so that the dot is centered, using the pencil eraser to poke the prongs through the silicone. FIG. 23 illustrates a depiction that may be used for inserting a prong snap. 11) Place the prong component, prong side up into the blue snap tool. Place a snap receptacle component over the prongs into the hole of the tool. 12) Hit the tool twice with a hammer. 13) Repeat until all four snaps have been placed. 14) Make silicone rings according to the following: retrieve 1/16" silicone sheeting, cut into 4"×36" strips; clean the silicone with 70% IPA wipes to remove all powder; on the poly cutting board, using the 3.5" punch over the silicone sheeting with at least 1/2 inch exposed on all sides and the rubber mallet, tap the leather punch on all sides of the punch at least twice; twist the punch on the silicone to ensure that the silicone is cut through; lift the punch and carefully remove the formed circle; on the poly cutting board, using the 3" punch over the 3.5" silicone circle, with 1/4" on all sides exposed, tap the punch with the rubber mallet at least twice on all sides; twist the leather punch on the silicone to ensure that the silicone is cut through; remove the 3" center portion and discard; remove the ring around the outside of the punch; use three rings for each patch; inspect each ring to ensure that it has a clear edge and all markings have been removed. 15) Attach rings to bottom assembly according to the following: turn the patch bottom component snap receptacle side down onto a space suitable for gluing; don gloves; retrieve Loctite 4011 from refrigerator; center cup onto patch bottom; glue silicone seals to patch bottom; place a small line of Loctite all around the outside of the cup. Place one silicone seal on the patch bottom, wiping up any excess glue as you go. Repeat for two more seals to make a total of 3/16" sides on the patch. 16) Inspect Patch bottom assembly to ensure that they are clean and cosmetically acceptable. 17) Add wires to bottom assembly according to the following: cut four one inch pieces of 28G wire, one for each color: red, black, white and green; solder to ring side of marked snap connectors: red to red, black to black, white to white and green to green; ensure all wires are soldered; make 3" wire cover label, using Avery label stock; punch 2 mm holes in wire cover label at center position of snaps; holding the wire cover label over the bottom assembly, pull all four wires through the prepared holes; remove the adhesive back and firmly affix to bottom of assembly; ensure that all four wires are pulled through and the label is cosmetically acceptable, evenly placed and without any wrinkles. FIG. 24 depicts a first illustration 2402 showing wires soldered to a bottom assembly, a second illustration 2404 showing a wire cover label, and a third illustration 2406 showing the wire cover affixed to the bottom assembly. 18) Add the HMI module to the bottom assembly according to the following: affix the HMI module to the bottom assembly using double sided foam tape. Ensure that the module antenna (blue) is as far away from the white wire snap connector as possible while the bottom of the module is as close to the green wire snap connector as possible without being on top of the snap connector; solder wires from bottom assembly to HMI module; verify that all the connections are solid. FIG. 25 illustrates a general view 2502 and detailed view 2504 of wire layout to the HMI module. 19) Prepare the switch and LED according to the following: short the LED cathode to 2.2K ohm resistor; bring the other side of the resistor out on a pin header; short the LED anode to pin 2 of the button switch and glue the LED to the right side wall of the switch; bring out a wire from pin 2 of the button switch on a pin header; bring out a wire from pin 1 of the button switch on a pin header. 20) Prepare the battery according to the following: add female pin header to red wire; add female pin header to black wire. 21) Add switch, led and battery to bottom assembly according to the following: arrange battery and switch on bottom assembly, with the writing on battery up; glue the LED to the side of the switch, ensuring that the LED still lights up; glue switch using Loctite 4011 to inside wall of seal ring, equidistant between the white and the black labeled wires/snaps; connect wires; secure battery under wires, bending corners as needed to fit into the circular bottom assembly; do not glue down the battery. FIG. 26 illustrates HMI module attached to the bottom assembly in a first illustration 2602 and switch, led, and battery attached to the bottom assembly in addition to the HMI module in a second illustration 2604. The design allows for battery replacement. 22) Load Patch driver according to the following: change the working directory to subdirectory "builds;" make sure button switch on Patch in off position; assemble hardware and setup; power on the supply. The LED on the Patch should glow and current consumption shown on the supply should be within 12 mA. If it is showing more than 50 mA, switch of the supply and debug. Make sure polarity of the cable connected from the supply to the adapter board is correct. From builds directory, execute the appropriate commands at the Linux prompt. The various hardware and setup necessary may include FT2232H Mini module (e.g., from Digikey); HIM Module to FTDI adapter (e.g., from Hmicro); Flat 10 finger flex cable (0.5 mm pitch) from Digikey; 3.6V supply; and USB cable—male A type to male Mini B type. 23) Load Adapter driver according to the following: assemble hardware and setup including adapter board 3.3 Version, dac Adapter board 2.0 Version, USB cable, and 5V DC wall power supply adapter; ensure jumper settings are; connect the USB cable to the PC from the adapter board; connect the 5V power supply from the board to the wall and turn on the power by pressing on the rocker switch; using the linux PC, from builds directory, execute the appropriate commands at the Linux prompt. If asked for password, give login password; turn off the adapter board by toggling the power switch; change the number 3 jumper setting such that both switches are moved to the left side; connect the DAC adapter board and ECG cable to the monitor; verify adapter board is ready to receive signals from the patch and display on the monitor; r Remember to turn on the adapter switch first and then switch on the patch. 23) Add top and finish Patch according to the following: prepare top using a 3.5" diameter punch, and punching a circle from 1/32" silicone sheet with adhesive on one side. Make a 5 mm hole at the position of the yellow button of the switch for the bottom assembly; prepare label using Uline S-19298 labels, print labels using laser printer and LBL-1008; punch label into 3" diameter circle; using prepared, punched top as a template, make a 5 mm hole at the position of the punched hole of the top. Ensure that top and label will align with the switch of the bottom assembly; using the bottom assembly, mark the position of the LED on the label. Use the 2 mm or similar punch to make a hole in the label for the LED; verify accuracy of prepared materials by aligning the top and label over the bottom assembly and checking the position of the punched holes over the switch and the LED. If the materials don't match, discard and start again; add label to top by removing the adhesive covering from the label and carefully placing the label on the top, moving from one side of the label to the other to prevent any air bubbles. Remove any small air bubbles. If air bubbles cannot be removed, replace label; remove the adhesive covering from the top and place it label side down (adhesive side up) on a table; using the backing from the label, cover the adhesive side of the top over the same position as the label. The effect is to have the silicone top in between the label and the label cover. The addition keeps the adhesive from sticking to the electronics; without touching the adhesive, place labeled top onto bottom assembly by first aligning the switch and then moving your fingers over the top to apply the top to the rings of the bottom assembly. 24) Final testing according to the following: place electrodes into all four snaps and if electrodes do not snap into place, reject the patch; inspect for any cosmetic defects (e.g., if label is smeared, reject, if top and bottom assembly do not align, reject, if there is excessive glue visible, reject); using the instructions for use, verify that the demo patch works (e.g., if the LED does not light up, reject, if the Patch does not pair with the adapter board, reject, if the ECG waveforms do not appear, reject). 25) Clean and package according to the following: prepare pouch label by using C 025 label stock and LBL-1006, make a pouch label; place label on pouch, carefully moving from one side of the pouch to the other and preventing air bubbles; clean Patch bottom and sides using slightly dampened C 006 70% IPA wipes. Do not wipe the label; allow to completely dry; place Patch in labeled pouch. FIG. 27 illustrates a patch label that may be placed on the patch.

The patch may be placed, tested, and used according to the following non-limiting instructions. 1) Patch Placement and Removal. a) Skin preparation: select an appropriate electrode site—either the upper left chest or center chest. Prepare the site by shaving or clipping any heavy hair. Open one of the prep pads and use light skin abrasion in the selected electrode site for best results. b) Prepare and place Patch—Remove Patch from the pouch. Attach electrodes into snap connectors, removing the covers from the electrode. Avoid touching the gel of the electrodes or placing them on any surface where they might stick. With yellow button of Patch towards the head and the button central and parallel to the long axis of the body, remove the covers from the electrodes (if not done already), and firmly press the Patch electrodes on the prepared site to assure uniform contact. For difficult areas such as hairy sites or contours (chest), use more downward pressure to increase adhesion. c) When testing is complete, turn off the Patch and remove by peeling away from the skin slowly. 2) Demonstration of Wireless Function. a) Prepare evaluation board and turn on. Connect 5 lead set to monitor cable. Connect leads to evaluation board. White (RA) to RA, green (RL) to RL, black (LA) to LA, and red (LL) to LL. Connect power cable to board and plug into standard outlet. Turn on the evaluation board by pressing the red rocker switch. Two green LEDs close to the rocker switch will light up to show that the board is turned on. b) Prepare monitor to receive signals. Turn on the monitor. Adjust settings as desired. c) Make signal connection. Turn on the Patch on the body by pressing the yellow button and ensuring that the red LED light is on while verifying that the yellow button is oriented toward the head, central and parallel to the long axis of the body and that all electrodes of the patch remain attached. Once the connection is secured, an LED to the right of the rocker switch will turn yellow-red. This may take a few seconds. d) The ECG will appear on the monitor. 3) Removal of the Patch and Equipment Shut Down. a) Remove Patch. Turn off the Patch by pressing the yellow button on the Patch. Note: this saves the battery life. Remove the Patch by peeling away from the skin slowly. Carefully remove the electrodes from the Patch by holding down the snap receptacle with your thumb and gently pulling the electrode from the receptacle. Note: The Patch may be removed and repositioned on the same person without changing electrodes. The electrodes are to be used by only one person. Each new person should have a new set of electrodes. Electrodes are disposable in regular trash. b) Shut down equipment. Turn off the evaluation board by pressing the red rocker button and unplugging the power supply. All LED indications will turn off. Turn off the monitor. 4) Cleaning and Reuse. To reuse the Patch, wipe down with 70% IPA wipes, dry and store in the original foil pouch.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An integrated patch comprising:
    a base comprising electrodes, wherein the electrodes are configured to gather information sufficient to generate at least three limb lead signals, wherein the base has a diameter of less than or equal to 5 inches;
    a cover coupled to the base;
    one or more non-electrode sensors configured to gather other information;
    an electronic module in communication with the electrodes, wherein the electronic module is housed between the base and the cover, wherein the electronic module comprises (i) a first instrumentation amplifier configured to receive and amplify signals from a first electrode and a second electrode of the electrodes to generate a first differential input signal and (ii) a second instrumentation amplifier configured to receive and amplify signals from a third electrode and the second electrode of the electrodes to generate a second differential input signal wherein the at least three limb lead signals are generated by calculating differentials between the first differential input signal, the second differential input signal, and a third input signal; and a radio in communication with the electronic module, the radio configured to wirelessly transmit or receive data.

2. The patch of claim 1, wherein the base comprises a fourth electrode configured to reduce a noise of acquired signals.

3. The patch of claim 2, wherein the base comprises a fifth electrode configured to reduce a noise of acquired signals, and wherein the fourth and fifth electrodes are located within at least 1.5 inches of each other.

4. The patch of claim 1, wherein the one or more non-electrode sensors comprise sensors configured to gather information regarding heart rate or respiration of a user.

5. The patch of claim 1, wherein the one or more non-electrode sensors comprise sensors configured to gather information regarding one or more members selected from the group consisting of (i) ambulatory data of a user, (ii) hydration, temperature, SpO2, or blood pressure of a user, and (iii) acceleration, audio, vision, or pressure of an environment around the patch.

6. The patch of claim 1, wherein the patch is configured to communicate with one or more external devices via the radio.

7. The patch of claim 6, wherein the one or more external devices comprise cell phones, tablet, PDAs, or fitness trackers.

8. The patch of claim 1, further comprising a spacer configured to separate the base from the cover, wherein the spacer defines a space in which the electronic module is to be located in.

9. The patch of claim 1, wherein the electronic module is removably coupled to the base.

10. The patch of claim 1, further comprising one or more processors individually or collectively configured to analyze or process gathered information.

11. The patch of claim 1, further comprising a visual, auditory, or haptic alert system configured to send an alert to a user based on gathered information.

12. The patch of claim 1, wherein the cover comprises one or more indicators associated with a preferred location or orientation of the patch.

13. The patch of claim 1, wherein four or fewer electrodes are arranged in a rectangular pattern and are configured to gather information sufficient to generate the at least three limb leads.

14. The patch of claim 12, wherein the one or more indicators visually respond to a correct placement of the patch on a user, thereby visually distinguishing between correct placement and incorrect placement of the patch on the user.

15. The patch of claim 12, wherein the preferred location is near a center of a chest or near an upper left chest of a human being.

16. A method of placing the integrated patch of claim 12 on a user comprising:
   matching the preferred location or orientation of the patch to a provided figure;
   placing the patch on the user at the preferred location or orientation.

17. The patch of claim 1, wherein the electronic module comprises fewer instrumentation amplifiers than a number of the electrodes, which fewer instrumentation amplifiers are configured to generate the at least three limb lead signals.

18. The patch of claim 1, wherein the electronic module comprises fewer instrumentation amplifiers than a number of the at least three limb lead signals generated.

19. The patch of claim 1, wherein the electronic module is configured to generate augmented limb lead signals.

20. The patch of claim 1, wherein the third input signal is zero.

* * * * *